US007678129B1

(12) United States Patent
Gesswein et al.

(10) Patent No.: US 7,678,129 B1
(45) Date of Patent: Mar. 16, 2010

(54) LOCKING COMPONENT FOR AN EMBOLIC FILTER ASSEMBLY

(75) Inventors: Douglas H. Gesswein, Temecula, CA (US); David K. Wrolstad, Temecula, CA (US); David H. Burkett, Temecula, CA (US); Robert C. Esselstein, Fallbrook, CA (US); Kathern J. Lind, Temecula, CA (US); Pablito Buan, Temecula, CA (US); Robert C. Hazelden, Temecula, CA (US); Thomas Tokarchik, III, Murrieta, CA (US); Ryan Grandfield, Murrieta, CA (US); Aaron Baldwin, Temecula, CA (US); Wayne E. Cornish, Fallbrook, CA (US); Philip S. Yip, San Jose, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 1351 days.

(21) Appl. No.: 10/805,455

(22) Filed: Mar. 19, 2004

(51) Int. Cl.
 *A61M 290/00* (2006.01)
(52) U.S. Cl. ..................... 606/200; 600/585
(58) Field of Classification Search ............... 606/159, 606/198, 200; 600/407, 433, 585, 434
 See application file for complete search history.

(56) References Cited

U.S. PATENT DOCUMENTS

| 3,952,747 A | 4/1976 | Kimmell, Jr. |
| 4,425,908 A | 1/1984 | Simon |
| 4,494,531 A | 1/1985 | Gianturco |
| 4,612,931 A | 9/1986 | Dormia |
| 4,619,246 A | 10/1986 | Molgaard-Nielsen et al. |
| 4,643,184 A | 2/1987 | Mobin-Uddin |
| 4,650,466 A | 3/1987 | Luther |
| 4,662,885 A | 5/1987 | DiPisa, Jr. |
| 4,688,553 A | 8/1987 | Metals |
| 4,706,671 A | 11/1987 | Weinrib |

(Continued)

FOREIGN PATENT DOCUMENTS

EP 0427429 A3 9/1991

(Continued)

OTHER PUBLICATIONS

Dilitation of the Carotid Artery By A Temporary Carotid Filter By A. Beck, St. Milic, A.M. Spagnoli, November.-December Issue of OPLITAI, an International Journal on Military Medicine and Health Emergencies, pp. 67-74.

(Continued)

*Primary Examiner*—Michael J Milano
*Assistant Examiner*—Victor X Nguyen
(74) *Attorney, Agent, or Firm*—Paul Y. Feng; Fulwider Patton LLP

(57) ABSTRACT

A locking component for locking a medical device onto a guide wire. Such medical devices include, for example, an embolic filter assembly used to capture embolic material that may be created and released into a patient's vasculature during a stenting or angioplasty procedure. The embolic filter assembly tracks along the guide wire, and is delivered to a treatment site where it is locked in place and deployed. The locking component enables the filter assembly to lock onto any standard guide wire, and does not require a modified guide wire that has a specially-designed fitting or stop to accomplish the locking function.

12 Claims, 10 Drawing Sheets

U.S. PATENT DOCUMENTS

| | | |
|---|---|---|
| 4,723,549 A | 2/1988 | Wholey et al. |
| 4,727,873 A | 3/1988 | Mobin-Uddin |
| 4,781,177 A | 11/1988 | Lebigot |
| 4,790,812 A | 12/1988 | Hawkins, Jr. et al. |
| 4,790,813 A | 12/1988 | Kensey |
| 4,794,928 A | 1/1989 | Kletschka |
| 4,832,055 A | 5/1989 | Palestrant |
| 4,873,978 A | 10/1989 | Ginsburg |
| 4,921,478 A | 5/1990 | Solano et al. |
| 4,921,484 A | 5/1990 | Hillstead |
| 4,969,891 A | 11/1990 | Gewertz |
| 4,990,156 A | 2/1991 | Lefebvre |
| 4,997,435 A | 3/1991 | Demeter |
| 4,998,539 A | 3/1991 | Delsanti |
| 5,053,008 A | 10/1991 | Bajaj |
| 5,064,428 A | 11/1991 | Cope et al. |
| 5,071,407 A | 12/1991 | Termin et al. |
| 5,092,839 A | 3/1992 | Kipperman |
| 5,100,423 A | 3/1992 | Fearnot |
| 5,100,425 A | 3/1992 | Fischell et al. |
| 5,102,415 A | 4/1992 | Guenther et al. |
| 5,108,419 A | 4/1992 | Reger et al. |
| 5,152,777 A | 10/1992 | Goldberg et al. |
| 5,158,548 A | 10/1992 | Lau |
| 5,160,342 A | 11/1992 | Reger et al. |
| 5,163,952 A | 11/1992 | Froix |
| 5,192,286 A | 3/1993 | Phan et al. |
| 5,324,304 A | 6/1994 | Rasmussen |
| 5,329,942 A | 7/1994 | Gunther et al. |
| 5,330,482 A | 7/1994 | Gibbs et al. |
| 5,350,398 A | 9/1994 | Pavcnik et al. |
| 5,370,657 A | 12/1994 | Irie |
| 5,375,612 A | 12/1994 | Cottenceau et al. |
| 5,383,887 A | 1/1995 | Nadal |
| 5,421,832 A | 6/1995 | Lefebvre |
| 5,490,859 A | 2/1996 | Mische et al. |
| 5,496,277 A | 3/1996 | Termin et al. |
| 5,496,330 A | 3/1996 | Bates et al. |
| 5,501,694 A | 3/1996 | Ressemann et al. |
| 5,549,626 A | 8/1996 | Miller et al. |
| 5,601,595 A | 2/1997 | Smith |
| 5,626,605 A | 5/1997 | Irie et al. |
| 5,634,942 A | 6/1997 | Chevillon et al. |
| 5,649,953 A | 7/1997 | Lefebvre |
| 5,658,296 A | 8/1997 | Bates et al. |
| 5,662,671 A | 9/1997 | Barbut et al. |
| 5,669,933 A | 9/1997 | Simon et al. |
| 5,681,347 A | 10/1997 | Cathcart et al. |
| 5,695,518 A | 12/1997 | Laerum |
| 5,695,519 A | 12/1997 | Summers et al. |
| 5,720,764 A | 2/1998 | Naderlinger |
| 5,725,550 A | 3/1998 | Nadal |
| 5,746,767 A | 5/1998 | Smith |
| 5,755,790 A | 5/1998 | Chevillon et al. |
| 5,759,192 A | 6/1998 | Saunders |
| 5,769,816 A | 6/1998 | Barbut et al. |
| 5,772,674 A | 6/1998 | Nakhjavan |
| 5,776,162 A | 7/1998 | Kleshinski |
| 5,779,716 A | 7/1998 | Cano et al. |
| 5,780,807 A | 7/1998 | Saunders |
| 5,792,145 A | 8/1998 | Bates et al. |
| 5,792,156 A | 8/1998 | Perouse |
| 5,792,157 A * | 8/1998 | Mische et al. ............... 606/159 |
| 5,795,322 A | 8/1998 | Boudewijn |
| 5,800,457 A | 9/1998 | Gelbfish |
| 5,800,525 A | 9/1998 | Bachinski et al. |
| 5,810,874 A | 9/1998 | Lefebvre |
| 5,814,064 A | 9/1998 | Daniel et al. |
| 5,827,324 A | 10/1998 | Cassell et al. |
| 5,833,650 A | 11/1998 | Imran |
| 5,836,868 A | 11/1998 | Ressemann et al. |
| 5,846,251 A | 12/1998 | Hart |
| 5,846,260 A | 12/1998 | Maahs |
| 5,848,964 A | 12/1998 | Samuels |
| 5,868,708 A | 2/1999 | Hart et al. |
| 5,876,367 A | 3/1999 | Kaganov et al. |
| 5,897,567 A | 4/1999 | Ressemann et al. |
| 5,910,154 A | 6/1999 | Tsugita et al. |
| 5,911,734 A | 6/1999 | Tsugita et al. |
| 5,935,139 A | 8/1999 | Bates |
| 5,941,869 A | 8/1999 | Patterson et al. |
| 5,941,896 A | 8/1999 | Kerr |
| 5,944,728 A | 8/1999 | Bates |
| 5,954,745 A | 9/1999 | Gertler et al. |
| 5,968,071 A | 10/1999 | Chevillon et al. |
| 5,976,172 A | 11/1999 | Homsma et al. |
| 5,980,555 A | 11/1999 | Barbut et al. |
| 5,989,281 A | 11/1999 | Barbut et al. |
| 6,001,118 A | 12/1999 | Daniel et al. |
| 6,007,557 A | 12/1999 | Ambrisco et al. |
| 6,013,093 A | 1/2000 | Nott et al. |
| 6,022,336 A | 2/2000 | Zadno-Azizi et al. |
| 6,027,520 A | 2/2000 | Tsugita et al. |
| 6,042,598 A | 3/2000 | Tsugita et al. |
| 6,051,015 A | 4/2000 | Maahs |
| 6,053,932 A | 4/2000 | Daniel et al. |
| 6,059,814 A | 5/2000 | Ladd |
| 6,066,158 A | 5/2000 | Engelson et al. |
| 6,074,357 A | 6/2000 | Kaganov et al. |
| 6,086,605 A | 7/2000 | Barbut et al. |
| 6,090,097 A | 7/2000 | Barbut et al. |
| 6,096,053 A | 8/2000 | Bates |
| 6,099,534 A | 8/2000 | Bates et al. |
| 6,099,549 A | 8/2000 | Bosma et al. |
| 6,117,154 A | 9/2000 | Barbut et al. |
| 6,129,739 A | 10/2000 | Khosravi |
| 6,131,266 A | 10/2000 | Saunders |
| 6,136,015 A | 10/2000 | Kurz |
| 6,136,016 A | 10/2000 | Barbut et al. |
| 6,142,987 A | 11/2000 | Tsugita |
| 6,152,946 A | 11/2000 | Broome et al. |
| 6,152,947 A | 11/2000 | Ambrisco et al. |
| 6,165,198 A | 12/2000 | McGurk et al. |
| 6,165,200 A | 12/2000 | Tsugita et al. |
| 6,168,579 B1 | 1/2001 | Tsugita et al. |
| 6,168,604 B1 | 1/2001 | Cano |
| 6,171,327 B1 | 1/2001 | Daniel et al. |
| 6,171,328 B1 | 1/2001 | Addis |
| 6,174,318 B1 | 1/2001 | Bates et al. |
| 6,176,849 B1 | 1/2001 | Yang et al. |
| 6,179,859 B1 | 1/2001 | Bates et al. |
| 6,179,860 B1 | 1/2001 | Fulton, III et al. |
| 6,179,861 B1 | 1/2001 | Khosravi et al. |
| 6,187,025 B1 | 2/2001 | Machek |
| 6,203,561 B1 | 3/2001 | Ramee et al. |
| 6,206,868 B1 | 3/2001 | Parodi |
| 6,209,710 B1 | 4/2001 | Mueller et al. |
| 6,214,026 B1 | 4/2001 | Lepak et al. |
| 6,224,620 B1 | 5/2001 | Maahs |
| 6,235,044 B1 | 5/2001 | Root et al. |
| 6,235,045 B1 | 5/2001 | Barbut et al. |
| 6,238,412 B1 | 5/2001 | Dubrul et al. |
| 6,241,746 B1 | 6/2001 | Bosma et al. |
| 6,245,012 B1 | 6/2001 | Kleshinski |
| 6,245,087 B1 | 6/2001 | Addis |
| 6,245,088 B1 | 6/2001 | Lowery |
| 6,245,089 B1 | 6/2001 | Daniel et al. |
| 6,251,122 B1 | 6/2001 | Tsukernik |
| 6,254,633 B1 | 7/2001 | Pinchuk et al. |
| 6,258,115 B1 | 7/2001 | Dubrul |
| 6,258,120 B1 | 7/2001 | McKenzie et al. |
| 6,264,663 B1 | 7/2001 | Cano |
| 6,264,672 B1 | 7/2001 | Fisher |
| 6,267,776 B1 | 7/2001 | O'Connell |

| | | |
|---|---|---|
| 6,267,777 B1 | 7/2001 | Bosma et al. |
| 6,270,477 B1 | 8/2001 | Bagaoisan et al. |
| 6,270,513 B1 | 8/2001 | Tsugita et al. |
| 6,273,901 B1 | 8/2001 | Whitcher et al. |
| 6,277,138 B1 | 8/2001 | Levinson et al. |
| 6,277,139 B1 | 8/2001 | Levinson et al. |
| 6,280,451 B1 | 8/2001 | Bates et al. |
| 6,287,321 B1 | 9/2001 | Jang |
| 6,290,656 B1 | 9/2001 | Boyle et al. |
| 6,295,989 B1 | 10/2001 | Connors, III |
| 6,306,163 B1 | 10/2001 | Fitz |
| 6,319,242 B1 | 11/2001 | Patterson et al. |
| 6,319,268 B1 | 11/2001 | Ambrisco et al. |
| 6,325,815 B1 | 12/2001 | Kusleika et al. |
| 6,336,934 B1 | 1/2002 | Gilson et al. |
| 6,340,364 B2 | 1/2002 | Kanesaka |
| 6,340,465 B1 | 1/2002 | Hsu et al. |
| 6,346,116 B1 | 2/2002 | Brooks et al. |
| 6,348,056 B1 | 2/2002 | Bates et al. |
| 6,355,051 B1 | 3/2002 | Sisskind et al. |
| 6,361,545 B1 | 3/2002 | Macoviak et al. |
| 6,361,546 B1 | 3/2002 | Khosravi |
| 6,364,895 B1 | 4/2002 | Greenhalgh |
| 6,364,896 B1 | 4/2002 | Addis |
| 6,371,969 B1 | 4/2002 | Tsugita et al. |
| 6,371,970 B1 | 4/2002 | Khosravi et al. |
| 6,371,971 B1 | 4/2002 | Tsugita et al. |
| 6,375,670 B1 | 4/2002 | Greenhalgh |
| 6,383,206 B1 | 5/2002 | Gillick et al. |
| 6,384,062 B1 | 5/2002 | Ikeda et al. |
| 6,391,044 B1 | 5/2002 | Yadav et al. |
| 6,394,978 B1 | 5/2002 | Boyle et al. |
| 6,395,014 B1 | 5/2002 | Macoviak et al. |
| 6,398,756 B2 | 6/2002 | Peterson et al. |
| 6,402,771 B1 | 6/2002 | Palmer et al. |
| 6,406,471 B1 | 6/2002 | Jang et al. |
| 6,423,032 B2 | 7/2002 | Parodi |
| 6,423,086 B1 | 7/2002 | Barbut et al. |
| 6,425,909 B1 | 7/2002 | Dieck et al. |
| 6,428,559 B1 | 8/2002 | Johnson |
| 6,432,122 B1 | 8/2002 | Gilson et al. |
| 6,436,121 B1 | 8/2002 | Blom |
| 6,443,926 B1 | 9/2002 | Kletschka |
| 6,443,971 B1 | 9/2002 | Boylan et al. |
| 6,443,972 B1 | 9/2002 | Bosma |
| 6,443,979 B1 | 9/2002 | Stalker et al. |
| 6,447,530 B1 | 9/2002 | Ostrovsky et al. |
| 6,447,531 B1 | 9/2002 | Amplatz |
| 6,450,989 B2 | 9/2002 | Dubrul et al. |
| 6,458,139 B1 | 10/2002 | Palmer et al. |
| 6,461,370 B1 | 10/2002 | Gray et al. |
| 6,468,291 B2 | 10/2002 | Bates et al. |
| 6,482,222 B1 | 11/2002 | Bruckheimer et al. |
| 6,485,456 B1 | 11/2002 | Kletschka |
| 6,485,497 B2 | 11/2002 | Wensel et al. |
| 6,485,500 B1 | 11/2002 | Kokish et al. |
| 6,485,501 B1 | 11/2002 | Green |
| 6,485,502 B2 | 11/2002 | Don Michael et al. |
| 6,485,507 B1 | 11/2002 | Walak et al. |
| 6,494,895 B2 | 12/2002 | Addis |
| 6,499,487 B1 | 12/2002 | McKenzie et al. |
| 6,500,166 B1 | 12/2002 | Zadno Azizi et al. |
| 6,506,203 B1 | 1/2003 | Boyle et al. |
| 6,506,205 B2 | 1/2003 | Goldberg et al. |
| 6,511,492 B1 | 1/2003 | Rosenbluth |
| 6,511,496 B1 | 1/2003 | Huter et al. |
| 6,511,497 B1 | 1/2003 | Braun et al. |
| 6,511,503 B1 | 1/2003 | Burkett et al. |
| 6,514,273 B1 | 2/2003 | Voss et al. |
| 6,517,550 B1 | 2/2003 | Konya et al. |
| 6,517,559 B1 | 2/2003 | O'Connell |
| 6,520,978 B1 | 2/2003 | Blackledge et al. |
| 6,527,746 B1 | 3/2003 | Oslund et al. |
| 6,527,791 B2 | 3/2003 | Fisher |
| 6,530,939 B1 | 3/2003 | Hopkins et al. |
| 6,530,940 B1 | 3/2003 | Fisher |
| 6,533,800 B1 | 3/2003 | Barbut |
| 6,537,294 B1 | 3/2003 | Boyle et al. |
| 6,537,295 B2 | 3/2003 | Peterson |
| 6,537,296 B2 | 3/2003 | Levinson et al. |
| 6,537,297 B2 | 3/2003 | Tsugita et al. |
| 6,540,722 B1 | 4/2003 | Boyle et al. |
| 6,540,767 B1 | 4/2003 | Walak et al. |
| 6,540,768 B1 | 4/2003 | Diaz et al. |
| 6,544,276 B1 | 4/2003 | Azizi |
| 6,544,279 B1 | 4/2003 | Hopkins et al. |
| 6,544,280 B1 | 4/2003 | Daniel et al. |
| 6,547,759 B1 | 4/2003 | Fisher |
| 6,551,268 B1 | 4/2003 | Kaganov et al. |
| 6,551,341 B2 | 4/2003 | Boylan et al. |
| 6,551,342 B1 | 4/2003 | Shen et al. |
| 6,558,401 B1 | 5/2003 | Azizi |
| 6,558,405 B1 | 5/2003 | McInnes |
| 6,562,058 B2 | 5/2003 | Seguin |
| 6,565,591 B2 | 5/2003 | Kelly et al. |
| 6,569,184 B2 | 5/2003 | Huter |
| 6,575,995 B1 | 6/2003 | Hunter et al. |
| 6,575,996 B1 | 6/2003 | Denison et al. |
| 6,575,997 B1 | 6/2003 | Palmer et al. |
| 6,582,447 B1 | 6/2003 | Patel et al. |
| 6,582,448 B1 | 6/2003 | Boyle et al. |
| 6,585,756 B1 | 7/2003 | Strecker |
| 6,589,263 B1 | 7/2003 | Hopkins et al. |
| 6,589,265 B1 | 7/2003 | Palmer et al. |
| 6,592,546 B1 | 7/2003 | Barbut et al. |
| 6,592,606 B2 | 7/2003 | Huter et al. |
| 6,592,607 B1 | 7/2003 | Palmer et al. |
| 6,592,616 B1 | 7/2003 | Stack et al. |
| 6,596,011 B2 | 7/2003 | Johnson et al. |
| 6,599,307 B1 | 7/2003 | Huter et al. |
| 6,599,308 B2 | 7/2003 | Amplatz |
| 6,602,269 B2 | 8/2003 | Wallace et al. |
| 6,602,271 B2 | 8/2003 | Adams et al. |
| 6,602,272 B2 | 8/2003 | Boylan et al. |
| 6,602,273 B2 | 8/2003 | Marshall |
| 6,605,102 B1 | 8/2003 | Mazzocchi et al. |
| 6,605,111 B2 | 8/2003 | Bose et al. |
| 6,607,506 B2 | 8/2003 | Kletschka |
| 6,610,077 B1 | 8/2003 | Hancock et al. |
| 6,616,679 B1 | 9/2003 | Khosravi et al. |
| 6,616,680 B1 | 9/2003 | Thielen |
| 6,616,681 B2 | 9/2003 | Hanson et al. |
| 6,616,682 B2 | 9/2003 | Joergensen et al. |
| 6,620,148 B1 | 9/2003 | Tsugita et al. |
| 6,620,182 B1 | 9/2003 | Khosravi |
| 6,623,450 B1 | 9/2003 | Dutta |
| 6,629,953 B1 | 10/2003 | Boyd |
| 6,632,236 B2 | 10/2003 | Hogendijk |
| 6,632,241 B1 | 10/2003 | Hancock et al. |
| 6,635,068 B1 | 10/2003 | Dubrul et al. |
| 6,635,070 B2 | 10/2003 | Evans et al. |
| 6,638,293 B1 | 10/2003 | Makowner et al. |
| 6,638,294 B1 | 10/2003 | Palmer |
| 6,645,220 B1 | 11/2003 | Huter et al. |
| 6,645,221 B1 | 11/2003 | Richter |
| 6,645,223 B2 | 11/2003 | Boyle et al. |
| 6,645,224 B2 | 11/2003 | Gilson et al. |
| 6,652,480 B1 | 11/2003 | Imran et al. |
| 6,652,505 B1 | 11/2003 | Tsugita et al. |
| 6,652,554 B1 | 11/2003 | Wholey et al. |
| 6,652,557 B1 | 11/2003 | MacDonald |
| 6,656,202 B2 | 12/2003 | Papp et al. |
| 6,656,203 B2 | 12/2003 | Roth et al. |
| 6,656,204 B2 | 12/2003 | Ambrisco et al. |
| 6,656,351 B2 | 12/2003 | Boyle |
| 6,660,021 B1 | 12/2003 | Palmer et al. |

| Patent | Date | Inventor |
|---|---|---|
| 6,663,650 B2 | 12/2003 | Sepetka et al. |
| 6,663,651 B2 | 12/2003 | Krolik et al. |
| 6,663,652 B2 | 12/2003 | Daniel et al. |
| 6,673,090 B2 | 1/2004 | Root et al. |
| 6,676,666 B2 | 1/2004 | Vrba et al. |
| 6,676,682 B1 | 1/2004 | Tsugita et al. |
| 6,676,683 B1 | 1/2004 | Addis |
| 6,679,902 B1 | 1/2004 | Boyle et al. |
| 6,679,903 B1 | 1/2004 | Kurz |
| 6,682,546 B2 | 1/2004 | Amplatz |
| 6,685,722 B1 | 2/2004 | Rosenbluth et al. |
| 6,689,151 B2 | 2/2004 | Becker et al. |
| 6,692,513 B2 | 2/2004 | Streeter et al. |
| 6,695,813 B1 | 2/2004 | Boyle et al. |
| 6,695,858 B1 | 2/2004 | Dubrul et al. |
| 6,695,864 B2 | 2/2004 | Macoviak et al. |
| 6,696,666 B2 | 2/2004 | Merdan et al. |
| 6,699,260 B2 | 3/2004 | Dubrul et al. |
| 6,702,834 B1 | 3/2004 | Boyle et al. |
| 6,706,055 B2 | 3/2004 | Douk et al. |
| 6,712,834 B2 | 3/2004 | Yassour et al. |
| 6,712,835 B2 | 3/2004 | Mazzocchi et al. |
| 6,716,231 B1 | 4/2004 | Rafiee et al. |
| 6,723,085 B2 | 4/2004 | Jang et al. |
| 6,726,701 B2 | 4/2004 | Gilson |
| 6,726,702 B2 | 4/2004 | Khosravi |
| 6,726,703 B2 | 4/2004 | Broome et al. |
| 6,740,061 B1 | 5/2004 | Oslund et al. |
| 6,743,247 B1 | 6/2004 | Levinson et al. |
| 6,746,469 B2 | 6/2004 | Mouw |
| 6,752,819 B1 | 6/2004 | Brady et al. |
| 6,755,846 B1 | 6/2004 | Yadav |
| 6,758,855 B2 | 7/2004 | Fulton, III et al. |
| 6,761,727 B1 | 7/2004 | Ladd |
| 6,773,448 B2 | 8/2004 | Kusleika et al. |
| 6,790,219 B1 | 9/2004 | Murphy |
| 6,793,666 B2 | 9/2004 | Hansen et al. |
| 6,793,668 B1 | 9/2004 | Fisher |
| 6,800,080 B1 | 10/2004 | Bates |
| 6,814,739 B2 | 11/2004 | Secrest et al. |
| 6,818,006 B2 | 11/2004 | Douk et al. |
| 6,837,898 B2 | 1/2005 | Boyle |
| 6,840,950 B2 | 1/2005 | Stanford et al. |
| 6,843,798 B2 | 1/2005 | Kusleika et al. |
| 6,846,316 B2 | 1/2005 | Abrams |
| 6,846,317 B1 | 1/2005 | Nigon |
| 6,863,696 B2 | 3/2005 | Kantsevitcha et al. |
| 6,866,677 B2 | 3/2005 | Douk et al. |
| 6,872,216 B2 | 3/2005 | Daniel et al. |
| 6,878,151 B2 | 4/2005 | Carrison et al. |
| 6,878,153 B2 | 4/2005 | Linder et al. |
| 6,887,256 B2 | 5/2005 | Gilson et al. |
| 6,887,257 B2 | 5/2005 | Salahieh et al. |
| 6,887,258 B2 | 5/2005 | Denison |
| 6,888,098 B1 | 5/2005 | Merdan et al. |
| 6,890,340 B2 | 5/2005 | Duane |
| 6,890,341 B2 | 5/2005 | Dieck et al. |
| 6,893,450 B2 | 5/2005 | Foster |
| 6,893,451 B2 | 5/2005 | Cano et al. |
| 6,896,690 B1 | 5/2005 | Lambrecht et al. |
| 6,896,691 B2 | 5/2005 | Boylan |
| 6,902,540 B2 | 6/2005 | Dorros et al. |
| 6,908,474 B2 | 6/2005 | Hogenkijk et al. |
| 6,911,036 B2 | 6/2005 | Douk et al. |
| 6,913,612 B2 | 7/2005 | Palmer et al. |
| 6,918,921 B2 | 7/2005 | Brady et al. |
| 6,929,652 B1 | 8/2005 | Andrews |
| 6,932,830 B2 | 8/2005 | Ungs |
| 6,932,831 B2 | 8/2005 | Forber |
| 6,936,058 B2 | 8/2005 | Forde et al. |
| 6,936,059 B2 | 8/2005 | Belef |
| 6,939,361 B1 | 9/2005 | Kleshinski |
| 6,939,362 B2 | 9/2005 | Boyle et al. |
| 6,942,673 B2 | 9/2005 | Bates et al. |
| 6,949,103 B2 | 9/2005 | Mazzocchi et al. |
| 6,951,570 B2 | 10/2005 | Linder et al. |
| 6,953,471 B1 | 10/2005 | Lilly et al. |
| 6,953,472 B2 | 10/2005 | Palmer et al. |
| 6,958,074 B2 | 10/2005 | Russell |
| 6,960,370 B2 | 11/2005 | Monni et al. |
| 6,962,598 B2 | 11/2005 | Linder et al. |
| 6,964,670 B1 | 11/2005 | Shah |
| 6,964,672 B2 | 11/2005 | Brady |
| 6,964,673 B2 | 11/2005 | Tsugita et al. |
| 6,969,395 B2 | 11/2005 | Eskuri |
| 6,969,396 B2 | 11/2005 | Krolik et al. |
| 6,969,402 B2 | 11/2005 | Bales et al. |
| 6,970,730 B2 | 11/2005 | Fuimaono et al. |
| 6,972,025 B2 | 12/2005 | WasDyke |
| 6,973,340 B2 | 12/2005 | Fuimaono et al. |
| 6,974,468 B2 | 12/2005 | DoBrava et al. |
| 6,974,469 B2 | 12/2005 | Broome et al. |
| 6,979,343 B2 | 12/2005 | Russo |
| 6,979,344 B2 | 12/2005 | Jones et al. |
| 6,986,778 B2 | 1/2006 | Zadno-Azizi |
| 6,989,021 B2 | 1/2006 | Bosma et al. |
| 6,989,027 B2 | 1/2006 | Allen et al. |
| 6,991,641 B2 | 1/2006 | Diaz et al. |
| 6,991,642 B2 | 1/2006 | Peterson |
| 9,989,019 | 1/2006 | Mazzo |
| RE38,972 E | 2/2006 | Purdy |
| 6,994,718 B2 | 2/2006 | Groothuis et al. |
| 6,997,938 B2 | 2/2006 | Wang et al. |
| 6,997,939 B2 | 2/2006 | Linder et al. |
| 7,001,406 B2 | 2/2006 | Eskuri et al. |
| 7,001,407 B2 | 2/2006 | Hansen et al. |
| 7,004,954 B1 | 2/2006 | Voss et al. |
| 7,004,955 B2 | 2/2006 | Shen et al. |
| 7,004,956 B2 | 2/2006 | Palmer et al. |
| 7,004,964 B2 | 2/2006 | Thompson et al. |
| 7,011,671 B2 | 3/2006 | Welch |
| 7,011,672 B2 | 3/2006 | Barbut et al. |
| 7,014,647 B2 | 3/2006 | Brady et al. |
| 7,018,372 B2 | 3/2006 | Casey |
| 7,018,385 B2 | 3/2006 | Bates et al. |
| 7,018,393 B1 | 3/2006 | Boyle et al. |
| 7,029,440 B2 | 4/2006 | Broome et al. |
| 7,033,375 B2 | 4/2006 | Mazzocchi et al. |
| 7,037,320 B2 | 5/2006 | Brady et al. |
| 7,041,116 B2 | 5/2006 | Goto et al. |
| 7,044,958 B2 | 5/2006 | Douk et al. |
| 7,048,752 B2 | 5/2006 | Mazzocchi |
| 7,048,758 B2 | 5/2006 | Boyle et al. |
| 7,056,328 B2 | 6/2006 | Arnott |
| 7,060,082 B2 | 6/2006 | Goll et al. |
| 7,077,854 B2 | 7/2006 | Khosravi |
| 7,094,243 B2 | 8/2006 | Mulholland |
| 7,094,249 B1 | 8/2006 | Broome et al. |
| 7,097,440 B2 | 8/2006 | Papp et al. |
| 7,097,651 B2 | 8/2006 | Harrison et al. |
| 7,101,379 B2 | 9/2006 | Gregory, Jr et al. |
| 7,101,380 B2 | 9/2006 | Khachin et al. |
| 7,108,707 B2 | 9/2006 | Huter et al. |
| 7,118,539 B2 * | 10/2006 | Vrba et al. ............ 600/585 |
| 2002/0015657 A1 | 2/2002 | Dong |
| 2002/0091408 A1 | 7/2002 | Sutton et al. |
| 2002/0091409 A1 | 7/2002 | Sutton et al. |
| 2002/0095141 A1 | 7/2002 | Belef et al. |
| 2002/0099407 A1 | 7/2002 | Becker et al. |
| 2002/0103501 A1 | 8/2002 | Diaz et al. |
| 2002/0107541 A1 | 8/2002 | Vale et al. |
| 2002/0111648 A1 | 8/2002 | Kusleika et al. |
| 2002/0111649 A1 | 8/2002 | Russo et al. |
| 2002/0115942 A1 | 8/2002 | Stanford et al. |
| 2002/0120286 A1 | 8/2002 | DoBrava et al. |
| 2002/0120287 A1 | 8/2002 | Huter |

| | | | | | |
|---|---|---|---|---|---|
| 2002/0121472 A1 | 9/2002 | Garner et al. | 2003/0135232 A1 | 7/2003 | Douk et al. |
| 2002/0123720 A1 | 9/2002 | Kusleika et al. | 2003/0139764 A1 | 7/2003 | Levinson et al. |
| 2002/0123755 A1 | 9/2002 | Lowe et al. | 2003/0144685 A1 | 7/2003 | Boyle et al. |
| 2002/0128679 A1 | 9/2002 | Turovskiy et al. | 2003/0150821 A1 | 8/2003 | Bates et al. |
| 2002/0128680 A1 | 9/2002 | Pavlovic | 2003/0153935 A1 | 8/2003 | Mialhe |
| 2002/0128681 A1 | 9/2002 | Broome et al. | 2003/0153942 A1 | 8/2003 | Wang et al. |
| 2002/0133092 A1 | 9/2002 | Oslund et al. | 2003/0153943 A1 | 8/2003 | Michael et al. |
| 2002/0138094 A1 | 9/2002 | Borillo et al. | 2003/0158574 A1 | 8/2003 | Esch et al. |
| 2002/0138095 A1 | 9/2002 | Mazzocchi et al. | 2003/0163064 A1 | 8/2003 | Vrba et al. |
| 2002/0143360 A1 | 10/2002 | Douk et al. | 2003/0171770 A1 | 9/2003 | Kusleika et al. |
| 2002/0143361 A1 | 10/2002 | Douk et al. | 2003/0171771 A1 | 9/2003 | Anderson et al. |
| 2002/0151927 A1 | 10/2002 | Douk et al. | 2003/0171803 A1 | 9/2003 | Shimon |
| 2002/0156456 A1 | 10/2002 | Fisher | 2003/0176884 A1 | 9/2003 | Berrada et al. |
| 2002/0161390 A1 | 10/2002 | Mouw | 2003/0176885 A1 | 9/2003 | Broome et al. |
| 2002/0161392 A1 | 10/2002 | Dubrul | 2003/0176886 A1 | 9/2003 | Wholey et al. |
| 2002/0161393 A1 | 10/2002 | Demond et al. | 2003/0176889 A1 | 9/2003 | Boyle et al. |
| 2002/0161395 A1 | 10/2002 | Douk et al. | 2003/0181942 A1 | 9/2003 | Sutton et al. |
| 2002/0165576 A1 | 11/2002 | Boyle et al. | 2003/0181943 A1 | 9/2003 | Daniel et al. |
| 2002/0169414 A1 | 11/2002 | Kletschka | 2003/0187474 A1 | 10/2003 | Keegan et al. |
| 2002/0169458 A1 | 11/2002 | Connors, III | 2003/0187475 A1 | 10/2003 | Tsugita et al. |
| 2002/0169472 A1 | 11/2002 | Douk et al. | 2003/0187495 A1 | 10/2003 | Cully et al. |
| 2002/0169474 A1 | 11/2002 | Kusleika et al. | 2003/0191493 A1 | 10/2003 | Epstein et al. |
| 2002/0173815 A1 | 11/2002 | Hogendijk et al. | 2003/0195554 A1 | 10/2003 | Shen et al. |
| 2002/0173817 A1 | 11/2002 | Kletschka et al. | 2003/0195555 A1 | 10/2003 | Khairkhahan et al. |
| 2002/0188313 A1 | 12/2002 | Johnson et al. | 2003/0195556 A1 | 10/2003 | Stack et al. |
| 2002/0188314 A1 | 12/2002 | Anderson et al. | 2003/0199819 A1 | 10/2003 | Beck |
| 2002/0193825 A1 | 12/2002 | McGuckin et al. | 2003/0199921 A1 | 10/2003 | Palmer et al. |
| 2002/0193826 A1 | 12/2002 | McGuckin et al. | 2003/0204168 A1 | 10/2003 | Bosme et al. |
| 2002/0193827 A1 | 12/2002 | McGuckin et al. | 2003/0204202 A1 | 10/2003 | Palmer et al. |
| 2002/0193828 A1 | 12/2002 | Griffin et al. | 2003/0208222 A1 | 11/2003 | Zadno-Azizi |
| 2003/0004536 A1 | 1/2003 | Boylan et al. | 2003/0208224 A1 | 11/2003 | Broome |
| 2003/0004537 A1 | 1/2003 | Boyle et al. | 2003/0208225 A1 | 11/2003 | Goll et al. |
| 2003/0004539 A1 | 1/2003 | Linder et al. | 2003/0208226 A1 | 11/2003 | Bruckheimer et al. |
| 2003/0004540 A1 | 1/2003 | Linder et al. | 2003/0208227 A1 | 11/2003 | Thomas |
| 2003/0004541 A1 | 1/2003 | Linder et al. | 2003/0208228 A1 | 11/2003 | Gilson et al. |
| 2003/0009188 A1 | 1/2003 | Linder et al. | 2003/0208229 A1 | 11/2003 | Kletschka |
| 2003/0009189 A1 | 1/2003 | Gilson et al. | 2003/0212361 A1 | 11/2003 | Boyle et al. |
| 2003/0015206 A1 | 1/2003 | Roth et al. | 2003/0212429 A1 | 11/2003 | Keegan et al. |
| 2003/0018354 A1 | 1/2003 | Roth et al. | 2003/0212431 A1 | 11/2003 | Brady et al. |
| 2003/0023265 A1 | 1/2003 | Forber | 2003/0212434 A1 | 11/2003 | Thielen |
| 2003/0028238 A1 | 2/2003 | Burkett et al. | 2003/0216774 A1 | 11/2003 | Larson |
| 2003/0032941 A1 | 2/2003 | Boyle et al. | 2003/0220665 A1 | 11/2003 | Eskuri et al. |
| 2003/0032977 A1 | 2/2003 | Brady et al. | 2003/0225418 A1 | 12/2003 | Eskuri et al. |
| 2003/0040772 A1 | 2/2003 | Hyodoh et al. | 2003/0225435 A1 | 12/2003 | Huter et al. |
| 2003/0042186 A1 | 3/2003 | Boyle et al. | 2003/0229295 A1 | 12/2003 | Houde et al. |
| 2003/0045898 A1 | 3/2003 | Harrison et al. | 2003/0229374 A1 | 12/2003 | Brady et al. |
| 2003/0057156 A1 | 3/2003 | Peterson et al. | 2003/0233117 A1 | 12/2003 | Adams et al. |
| 2003/0060782 A1 | 3/2003 | Bose et al. | 2003/0236545 A1 | 12/2003 | Gilson |
| 2003/0060843 A1 | 3/2003 | Boucher | 2004/0002730 A1 | 1/2004 | Denison et al. |
| 2003/0060844 A1 | 3/2003 | Borillo et al. | 2004/0006361 A1 | 1/2004 | Boyle et al. |
| 2003/0065354 A1 | 4/2003 | Boyle et al. | 2004/0006364 A1 | 1/2004 | Ladd |
| 2003/0069596 A1 | 4/2003 | Eskuri | 2004/0006365 A1 | 1/2004 | Brady et al. |
| 2003/0069597 A1 | 4/2003 | Petersen | 2004/0006366 A1 | 1/2004 | Huter et al. |
| 2003/0078519 A1 | 4/2003 | Salahieh et al. | 2004/0006367 A1 | 1/2004 | Johnson et al. |
| 2003/0078614 A1 | 4/2003 | Salahieh et al. | 2004/0006368 A1 | 1/2004 | Mazzocchi et al. |
| 2003/0083692 A1 | 5/2003 | Vrba et al. | 2004/0015184 A1 | 1/2004 | Boyle et al. |
| 2003/0083693 A1 | 5/2003 | Daniel et al. | 2004/0019363 A1 | 1/2004 | Hanson et al. |
| 2003/0100917 A1 | 5/2003 | Boyle et al. | 2004/0034385 A1 | 2/2004 | Gilson et al. |
| 2003/0100918 A1 | 5/2003 | Duane | 2004/0039411 A1 | 2/2004 | Gilson et al. |
| 2003/0105484 A1 | 6/2003 | Boyle et al. | 2004/0044359 A1 | 3/2004 | Renati et al. |
| 2003/0109824 A1 | 6/2003 | Anderson et al. | 2004/0044360 A1 | 3/2004 | Lowe |
| 2003/0114879 A1 | 6/2003 | Euteneuer et al. | 2004/0049226 A1 | 3/2004 | Keegan et al. |
| 2003/0114880 A1 | 6/2003 | Hansen et al. | 2004/0059372 A1 | 3/2004 | Tsugita |
| 2003/0120303 A1 | 6/2003 | Boyle et al. | 2004/0059373 A1 | 3/2004 | Shapiro et al. |
| 2003/0130680 A1 | 7/2003 | Russell | 2004/0082967 A1 | 4/2004 | Broome et al. |
| 2003/0130681 A1 | 7/2003 | Ungs | 2004/0082968 A1 | 4/2004 | Krolik et al. |
| 2003/0130682 A1 | 7/2003 | Broome et al. | 2004/0088000 A1 | 5/2004 | Muller |
| 2003/0130684 A1 | 7/2003 | Brady et al. | 2004/0088002 A1 | 5/2004 | Boyle et al. |
| 2003/0130685 A1 | 7/2003 | Daniel et al. | 2004/0093009 A1 | 5/2004 | Denison et al. |
| 2003/0130686 A1 | 7/2003 | Daniel et al. | 2004/0093010 A1 | 5/2004 | Gesswein et al. |
| 2003/0130687 A1 | 7/2003 | Daniel et al. | 2004/0093011 A1 | 5/2004 | Vrba |
| 2003/0130688 A1 | 7/2003 | Daniel et al. | 2004/0093012 A1 | 5/2004 | Cully et al. |
| 2003/0135162 A1 | 7/2003 | Deyette, Jr. et al. | 2004/0093013 A1 | 5/2004 | Brady et al. |

| | | |
|---|---|---|
| 2004/0098022 A1 | 5/2004 | Barone |
| 2004/0098026 A1 | 5/2004 | Joergensen et al. |
| 2004/0098032 A1 | 5/2004 | Papp et al. |
| 2004/0098033 A1 | 5/2004 | Leeflang et al. |
| 2004/0102807 A1 | 5/2004 | Kusleika et al. |
| 2004/0106944 A1 | 6/2004 | Daniel et al. |
| 2004/0111111 A1 | 6/2004 | Lin |
| 2004/0116960 A1 | 6/2004 | Demond et al. |
| 2004/0122466 A1 | 6/2004 | Bales |
| 2004/0127933 A1 | 7/2004 | Demond et al. |
| 2004/0127934 A1 | 7/2004 | Gilson et al. |
| 2004/0127936 A1 | 7/2004 | Salaheih et al. |
| 2004/0138693 A1 | 7/2004 | Eskuri et al. |
| 2004/0138694 A1 | 7/2004 | Tran et al. |
| 2004/0138696 A1 | 7/2004 | Drasler et al. |
| 2004/0144689 A1 | 7/2004 | Berlowitz et al. |
| 2004/0147955 A1 | 7/2004 | Beulke et al. |
| 2004/0153118 A1 | 8/2004 | Clubb et al. |
| 2004/0153119 A1 | 8/2004 | Kusleika et al. |
| 2004/0158275 A1 | 8/2004 | Crank et al. |
| 2004/0158277 A1 | 8/2004 | Lowe et al. |
| 2004/0158278 A1 | 8/2004 | Becker et al. |
| 2004/0158279 A1 | 8/2004 | Petersen |
| 2004/0158280 A1 | 8/2004 | Morris et al. |
| 2004/0158281 A1 | 8/2004 | Boylan et al. |
| 2004/0167564 A1 | 8/2004 | Fedie |
| 2004/0167565 A1 | 8/2004 | Beulke et al. |
| 2004/0167566 A1 | 8/2004 | Beulke et al. |
| 2004/0167567 A1 | 8/2004 | Cano et al. |
| 2004/0167568 A1 | 8/2004 | Boylan et al. |
| 2004/0172055 A1 | 9/2004 | Huter et al. |
| 2004/0176794 A1 | 9/2004 | Khosravi |
| 2004/0193208 A1 | 9/2004 | Talpade et al. |
| 2004/0199198 A1 | 10/2004 | Beulke et al. |
| 2004/0199199 A1 | 10/2004 | Krolik et al. |
| 2004/0199203 A1 | 10/2004 | Oslund et al. |
| 2004/0204737 A1 | 10/2004 | Boismier et al. |
| 2004/0210250 A1 | 10/2004 | Eskuri |
| 2004/0220608 A1 | 11/2004 | D'Aquanni et al. |
| 2004/0220609 A1 | 11/2004 | Douk et al. |
| 2004/0220611 A1 | 11/2004 | Ogle |
| 2004/0225322 A1 | 11/2004 | Garrison et al. |
| 2004/0236368 A1 | 11/2004 | McGucklin, Jr. et al. |
| 2004/0236369 A1 | 11/2004 | Dubrul |
| 2004/0249409 A1 | 12/2004 | Krolik et al. |
| 2004/0254601 A1 | 12/2004 | Eskuri |
| 2004/0254602 A1 | 12/2004 | Lehe et al. |
| 2004/0260308 A1 | 12/2004 | Gilson et al. |
| 2004/0260333 A1 | 12/2004 | Dubrul et al. |
| 2004/0267301 A1 | 12/2004 | Boylan et al. |
| 2004/0267302 A1 | 12/2004 | Gilson et al. |
| 2005/0004594 A1 | 1/2005 | Nool et al. |
| 2005/0004595 A1 | 1/2005 | Boyle et al. |
| 2005/0004597 A1 | 1/2005 | McGuckin et al. |
| 2005/0010245 A1 | 1/2005 | Wasicek |
| 2005/0010246 A1 | 1/2005 | Steeter et al. |
| 2005/0010247 A1 | 1/2005 | Kusleika et al. |
| 2005/0021075 A1 | 1/2005 | Bonnette et al. |
| 2005/0021076 A1 | 1/2005 | Mazzocchi et al. |
| 2005/0055048 A1 | 3/2005 | Dieck et al. |
| 2005/0070953 A1 | 3/2005 | Riley |
| 2005/0075663 A1 | 4/2005 | Boyle et al. |
| 2005/0080446 A1 | 4/2005 | Gilson et al. |
| 2005/0085842 A1 | 4/2005 | Eversull et al. |
| 2005/0090845 A1 | 4/2005 | Boyd |
| 2005/0090857 A1 | 4/2005 | Kusleika et al. |
| 2005/0090858 A1 | 4/2005 | Pavlovic |
| 2005/0096691 A1 | 5/2005 | Groothuis et al. |
| 2005/0096692 A1 | 5/2005 | Linder et al. |
| 2005/0101986 A1 | 5/2005 | Daniel et al. |
| 2005/0101987 A1 | 5/2005 | Salahieh |
| 2005/0101988 A1 | 5/2005 | Stanford et al. |
| 2005/0101989 A1 | 5/2005 | Cully et al. |
| 2005/0113865 A1 | 5/2005 | Daniel et al. |
| 2005/0119688 A1 | 6/2005 | Bergheim |
| 2005/0119689 A1 | 6/2005 | Mazzocchi et al. |
| 2005/0119690 A1 | 6/2005 | Mazzocchi et al. |
| 2005/0119691 A1 | 6/2005 | Daniel et al. |
| 2005/0124931 A1 | 6/2005 | Fulton et al. |
| 2005/0125023 A1 | 6/2005 | Bates et al. |
| 2005/0131450 A1 | 6/2005 | Nicholson et al. |
| 2005/0131453 A1 | 6/2005 | Parodi |
| 2005/0149110 A1 | 7/2005 | Wholey et al. |
| 2005/0149112 A1 | 7/2005 | Barbut |
| 2005/0149113 A1 | 7/2005 | Douk et al. |
| 2005/0159772 A1 | 7/2005 | Lowe et al. |
| 2005/0159773 A1 | 7/2005 | Broome et al. |
| 2005/0159774 A1 | 7/2005 | Belef |
| 2005/0171573 A1 | 8/2005 | Salahieh et al. |
| 2005/0177187 A1 | 8/2005 | Gray et al. |
| 2005/0182440 A1 | 8/2005 | Bates et al. |
| 2005/0182441 A1 | 8/2005 | Denison et al. |
| 2005/0192623 A1 | 9/2005 | Mazzocchi et al. |
| 2005/0192624 A1 | 9/2005 | Mazzocchi et al. |
| 2005/0203567 A1 | 9/2005 | Linder et al. |
| 2005/0203568 A1 | 9/2005 | Burg et al. |
| 2005/0203569 A1 | 9/2005 | Kusleika et al. |
| 2005/0203570 A1 | 9/2005 | Mazzocchi et al. |
| 2005/0203571 A1 | 9/2005 | Mazzocchi et al. |
| 2005/0209634 A1 | 9/2005 | Brady et al. |
| 2005/0209635 A1 | 9/2005 | Gilson et al. |
| 2005/0216051 A1 | 9/2005 | Mazzocchi et al. |
| 2005/0216052 A1 | 9/2005 | Mazzocchi et al. |
| 2005/0216053 A1 | 9/2005 | Douk et al. |
| 2005/0222583 A1 | 10/2005 | Cano et al. |
| 2005/0222604 A1 | 10/2005 | Schaeffer et al. |
| 2005/0222607 A1 | 10/2005 | Palmer et al. |
| 2005/0228437 A1 | 10/2005 | Gilson et al. |
| 2005/0228438 A1 | 10/2005 | Sachar et al. |
| 2005/0228439 A1 | 10/2005 | Andrews et al. |
| 2005/0234502 A1 | 10/2005 | Gilson et al. |
| 2005/0240215 A1 | 10/2005 | Ellis |
| 2005/0245866 A1 | 11/2005 | Azizi |
| 2005/0267517 A1 | 12/2005 | Ungs |
| 2005/0283184 A1 | 12/2005 | Gilson et al. |
| 2005/0283185 A1 | 12/2005 | Linder et al. |
| 2005/0283186 A1 | 12/2005 | Berrada et al. |
| 2005/0288705 A1 | 12/2005 | Gilson et al. |
| 2006/0004403 A1 | 1/2006 | Gilson et al. |
| 2006/0004405 A1 | 1/2006 | Salaheih et al. |
| 2006/0015138 A1 | 1/2006 | Gertner et al. |
| 2006/0015139 A1 | 1/2006 | Tsugita et al. |
| 2006/0015140 A1 | 1/2006 | Tsugita et al. |
| 2006/0015141 A1 | 1/2006 | Linder et al. |
| 2006/0020286 A1 | 1/2006 | Niermann |
| 2006/0025803 A1 | 2/2006 | Mitelberg et al. |
| 2006/0025804 A1 | 2/2006 | Krolik et al. |
| 2006/0025805 A1 | 2/2006 | DoBrava et al. |
| 2006/0030876 A1 | 2/2006 | Peacock, III et al. |
| 2006/0030877 A1 | 2/2006 | Martinez et al. |
| 2006/0030878 A1 | 2/2006 | Anderson et al. |
| 2006/0052817 A1 | 3/2006 | Russo et al. |
| 2006/0074446 A1 | 4/2006 | Gilson et al. |
| 2006/0095069 A1 | 5/2006 | Shah et al. |
| 2006/0100659 A1 | 5/2006 | Dinh et al. |
| 2006/0100662 A1 | 5/2006 | Daniel et al. |
| 2006/0100663 A1 | 5/2006 | Palmer et al. |
| 2006/0116715 A1 | 6/2006 | Khosravi et al. |
| 2006/0122643 A1 | 6/2006 | Wasicek |
| 2006/0122644 A1 | 6/2006 | Brady et al. |
| 2006/0122645 A1 | 6/2006 | Brady et al. |
| 2006/0129181 A1 | 6/2006 | Callol et al. |
| 2006/0129182 A1 | 6/2006 | Gilson et al. |
| 2006/0129183 A1 | 6/2006 | Boyle et al. |
| 2006/0149312 A1 | 7/2006 | Arguello et al. |
| 2006/0149313 A1 | 7/2006 | Arguello et al. |

| | | | | | | |
|---|---|---|---|---|---|---|
| 2006/0149314 A1 | 7/2006 | Borillo et al. | | WO | WO96/01591 | 1/1996 |
| 2006/0155322 A1 | 7/2006 | Sater et al. | | WO | WO97/17100 | 5/1997 |
| 2006/0161198 A1 | 7/2006 | Sakai et al. | | WO | WO98/02084 | 1/1998 |
| 2006/0167491 A1 | 7/2006 | Wholey et al. | | WO | WO98/33443 | 8/1998 |
| 2006/0184194 A1 | 8/2006 | Pal et al. | | WO | WO99/23976 | 5/1999 |
| 2006/0190025 A1 | 8/2006 | Lehe et al. | | WO | WO99/44510 | 9/1999 |
| 2006/0195137 A1 | 8/2006 | Sepetka et al. | | WO | WO00/67667 | 11/2000 |
| 2006/0195138 A1 | 8/2006 | Goll et al. | | WO | WO01/10346 | 2/2001 |
| 2006/0200047 A1 | 9/2006 | Galdonik et al. | | WO | WO01/45592 | 6/2001 |
| 2006/0200191 A1 | 9/2006 | Zadno-Azizi | | WO | WO01/87183 | 11/2001 |
| 2006/0206139 A1 | 9/2006 | Tekulve | | | | |
| 2007/0162071 A1* | 7/2007 | Burkett et al. ............... 606/200 | | | | |

FOREIGN PATENT DOCUMENTS

| | | |
|---|---|---|
| EP | 0 472 334 A1 | 2/1992 |
| EP | 0533511 A1 | 3/1993 |
| FR | 2580504 A1 | 10/1986 |
| GB | 2020557 | 11/1979 |
| WO | WO92/03097 | 3/1992 |

OTHER PUBLICATIONS

Tsugita, Ross et al., *Guidewire Filter And Methods Of Use*, U.S. Appl. No. 10/080,770, filed Feb. 22, 2002; Publication No. 2002/0095174 Al, Jul. 18, 2002.

Schetky, L. McDonald, *Shape-Memory Alloys*, Scientific American, vol. 281, pp. 74-82 (Nov. 1979).

\* cited by examiner

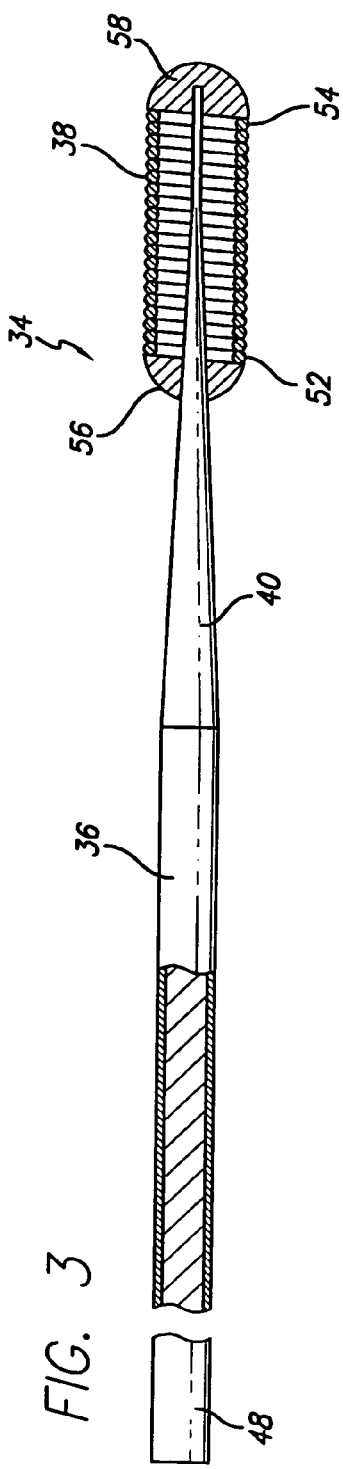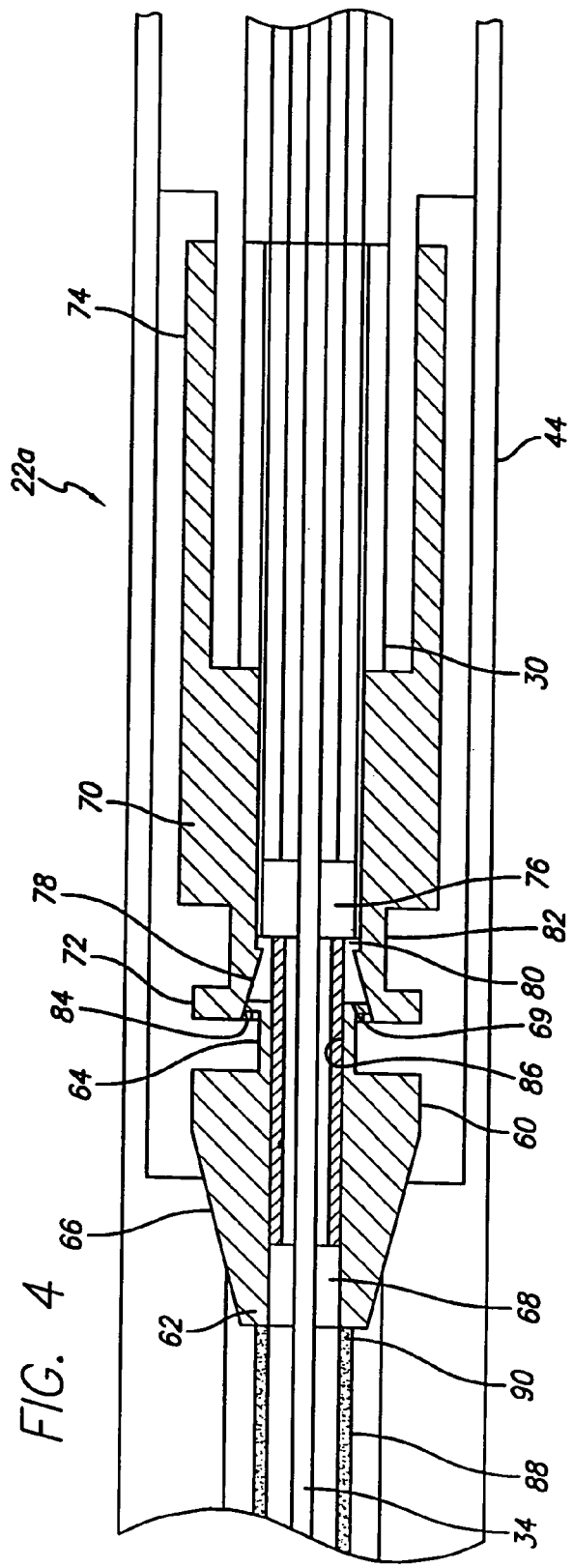

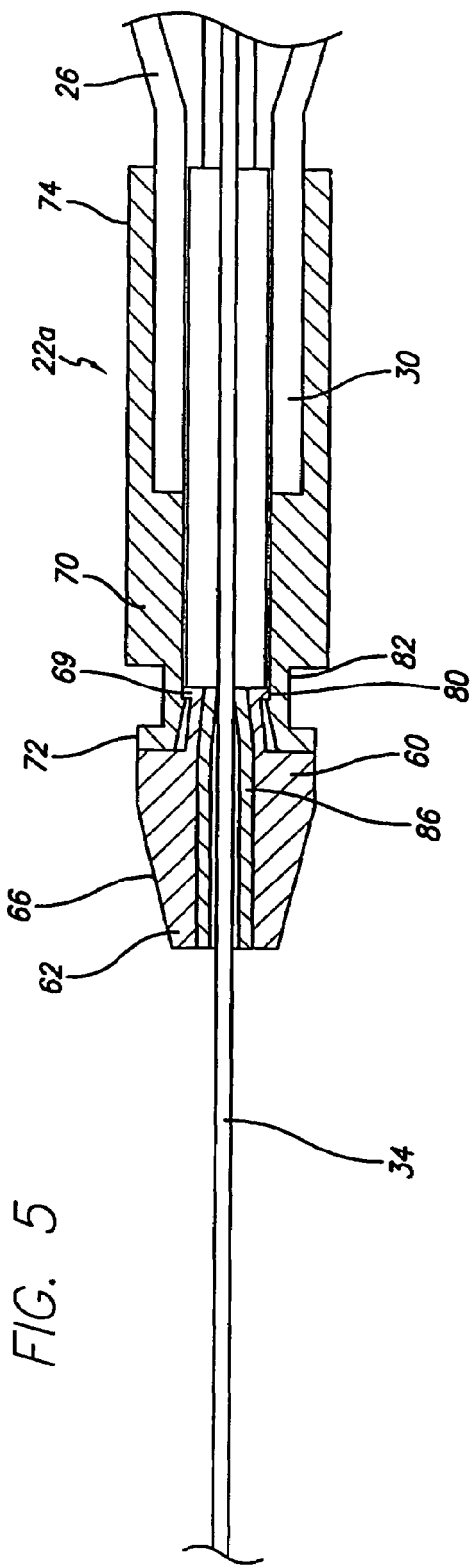
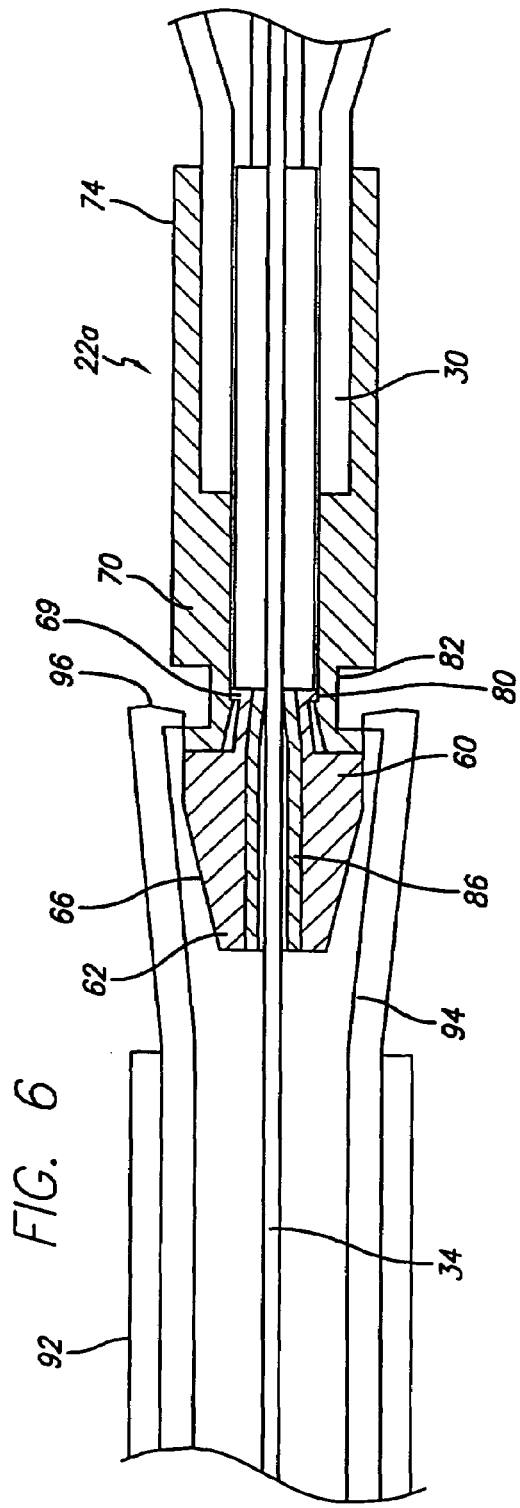
FIG. 5
FIG. 6

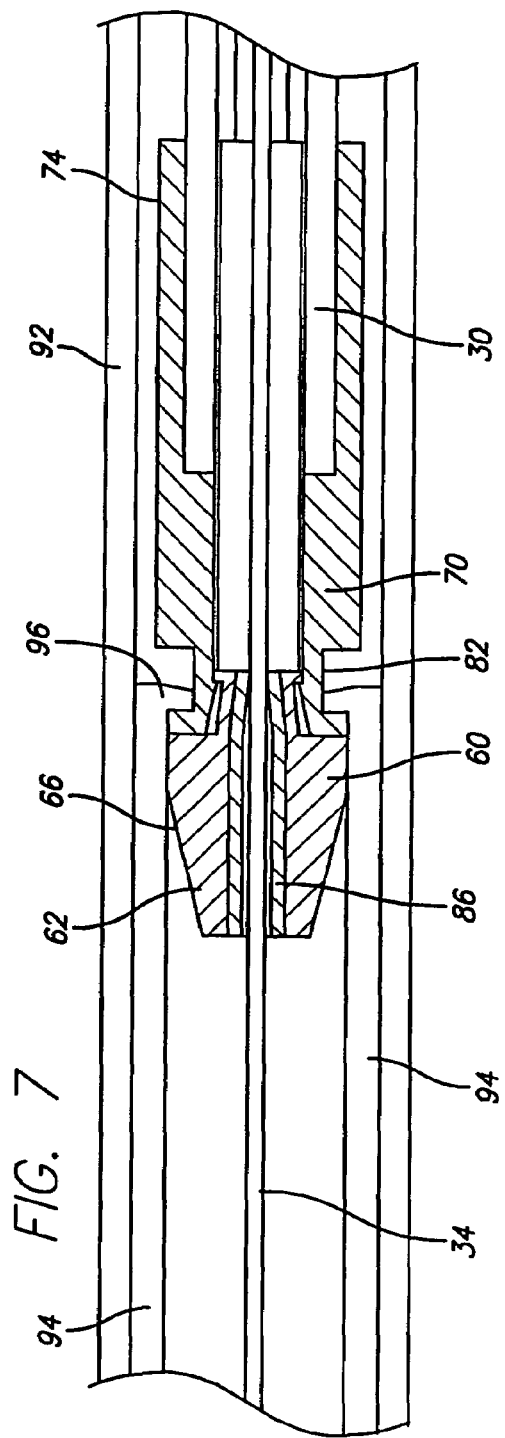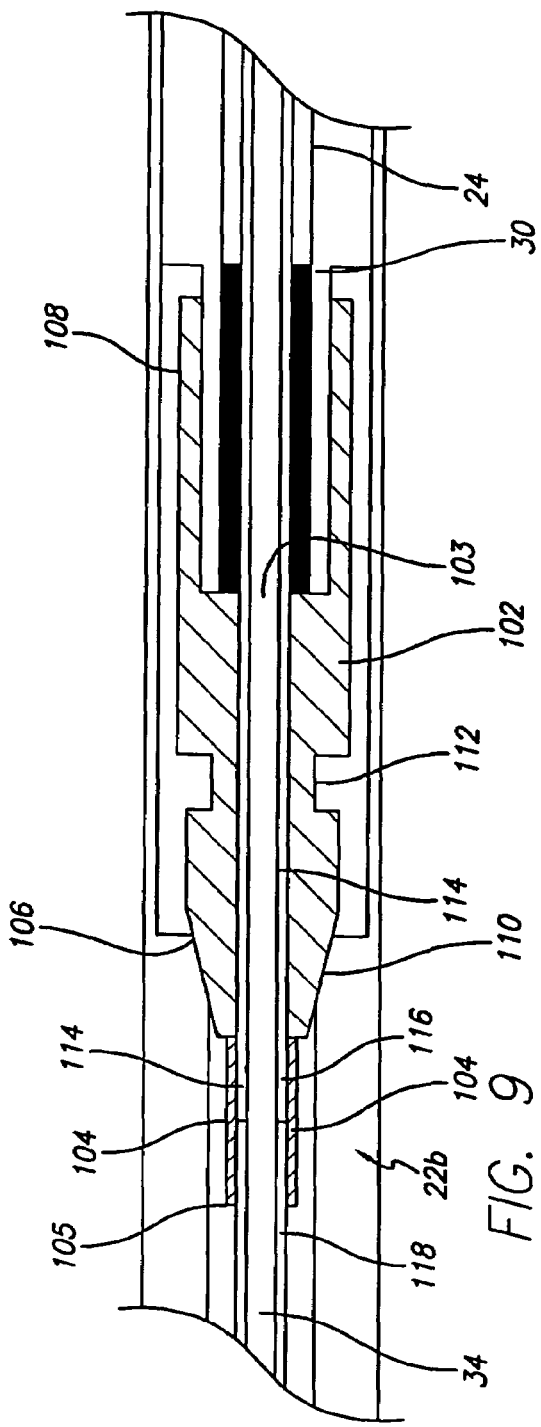

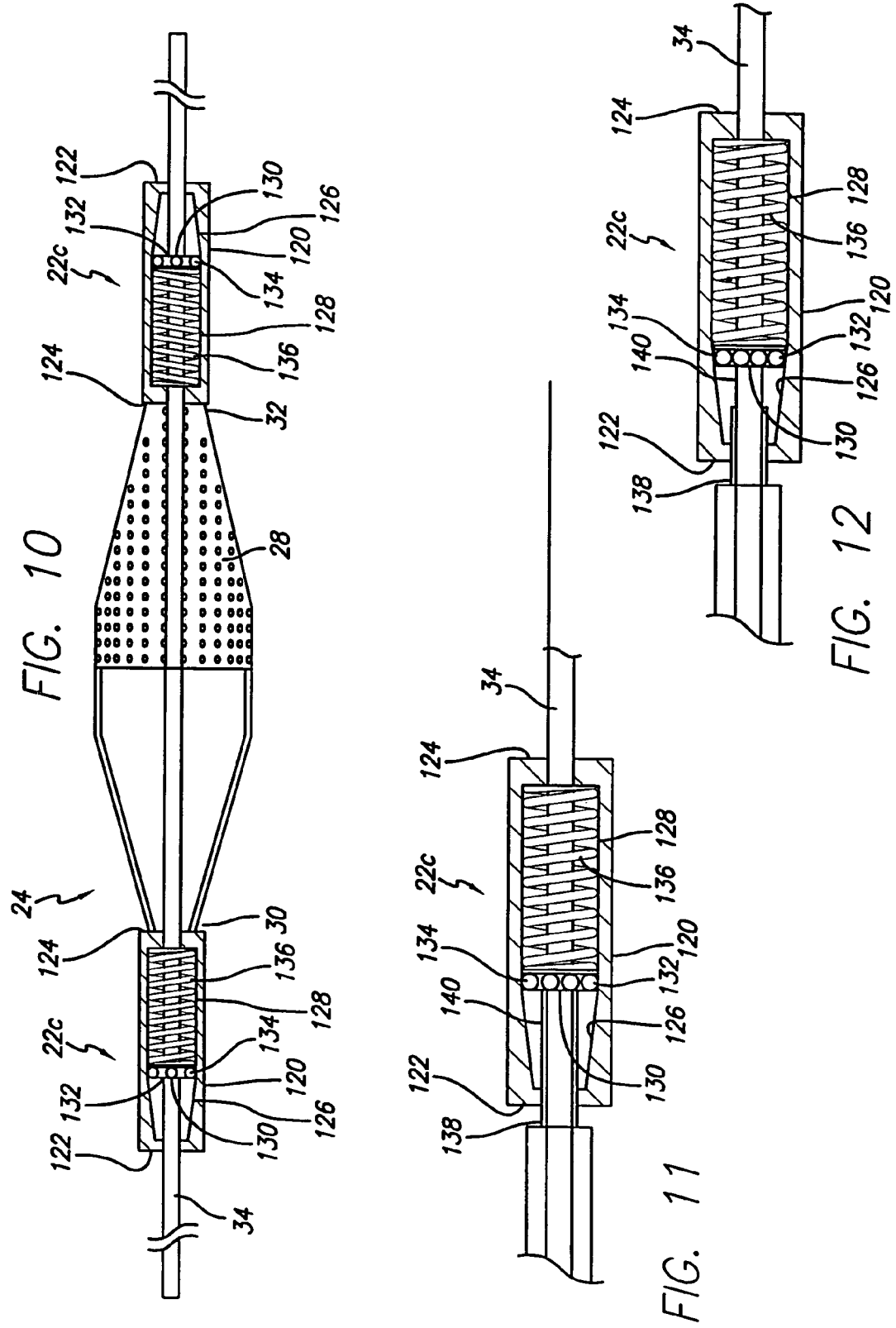

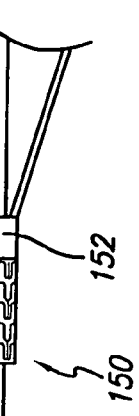
FIG. 13a
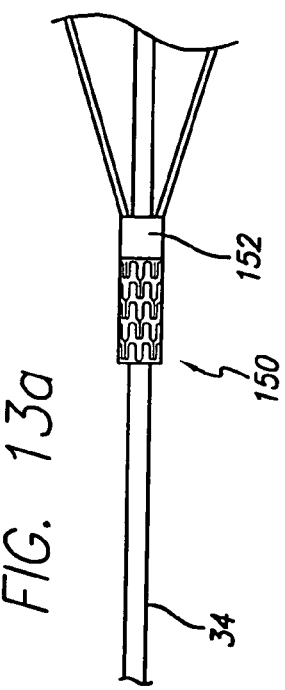
FIG. 13
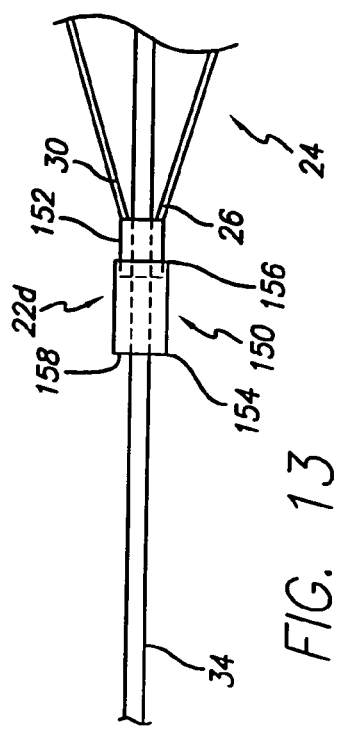
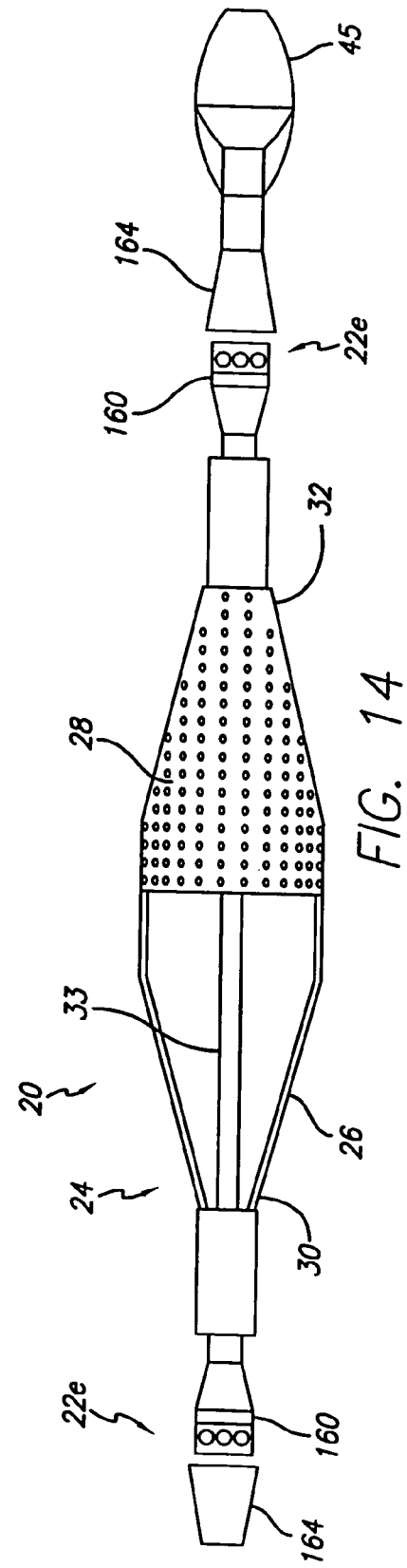
FIG. 14

LOCKING COMPONENT FOR AN EMBOLIC FILTER ASSEMBLY

BACKGROUND OF THE INVENTION

The present invention relates generally to medical devices used to perform interventional procedures in a patient's vasculature, which can be delivered through a body lumen via a steerable guide wire and into an area of treatment such as, for example, a stenosed or occluded region of an artery or other body vessel. The present invention is more particularly directed to a locking component disposed on a medical device to allow the medical device to be delivered along the guide wire to the treatment area and locked in place. The locking component of the present invention is intended for use on a standard guide wire of the physician's choice, and does not require a modified guide wire with specially-designed stops or other mechanisms to accomplish the locking function.

Numerous medical procedures have been devised for treating occluded blood vessels to allow blood to flow without obstruction. Such procedures usually involve the percutaneous introduction of an interventional device into the lumen of the artery, usually by a catheter. One widely known and medically accepted procedure is balloon angioplasty in which an inflatable balloon is introduced within the stenosed region of the blood vessel to dilate the occluded vessel. The balloon dilatation catheter is initially inserted into the patient's arterial system and is advanced and manipulated into the area of stenosis in the artery. The balloon is inflated to compress the plaque and press the vessel wall radially outward to increase the diameter of the blood vessel, resulting in increased blood flow. The balloon is then deflated to a small profile so that the dilatation catheter can be withdrawn from the patient's vasculature and the blood flow resumed through the dilated artery. As should be appreciated by those skilled in the art, while the above described procedure is typical, it is not the only method used in angioplasty.

Another procedure is laser angioplasty which uses a laser to ablate the stenosis by super heating and vaporizing the deposited plaque. Atherectomy is yet another method of treating a stenosed body vessel in which cutting blades are rotated to shave the deposited plaque from the arterial wall. A vacuum catheter is usually used to capture the shaved plaque or thrombus from the blood stream during this procedure.

In the procedures of the kind referenced above, abrupt reclosure may occur or restenosis of the artery may develop over time, which may require another angioplasty procedure, a surgical bypass operation, or some other method of repairing or strengthening the area. To reduce the likelihood of the occurrence of reclosure and to strengthen the area, a physician can implant an intravascular prosthesis for maintaining vascular patency, commonly known as a stent, inside the artery across the lesion. The stent can be crimped tightly onto the balloon portion of the catheter and transported in its delivery diameter through the patient's vasculature. At the deployment site, the stent is expanded to a larger diameter, often by inflating the balloon portion of the catheter.

The above non-surgical interventional procedures, when successful, avoid the necessity of major surgical operations. However, there is one common problem which can become associated with all of these non-surgical procedures, namely, the potential release of embolic debris into the bloodstream that can occlude distal vasculature and cause significant health problems to the patient. For example, during deployment of a stent, it is possible that the metal struts of the stent can cut into the stenosis and create particles of plaque that can travel downstream and lodge somewhere in the patient's vascular system. Pieces of plaque material are sometimes generated during a balloon angioplasty procedure and are released into the bloodstream. Additionally, while complete vaporization of plaque is the intended goal during laser angioplasty, sometimes particles are not fully vaporized and enter the bloodstream. Likewise, not all of the emboli created during an atherectomy procedure may be drawn into the vacuum catheter and, as a result, may enter the bloodstream as well.

When any of the above described procedures are performed in the carotid arteries, the release of emboli into the circulatory system can be extremely dangerous and sometimes fatal to the patient. Debris carried by the bloodstream to distal vessels of the brain can cause cerebral vessels to occlude, resulting in a stroke, and in some cases, death. Therefore, although cerebral percutaneous transluminal angioplasty has been performed in the past, the number of procedures performed has been somewhat limited due to the justifiable fear of an embolic stroke occurring should embolic debris enter the bloodstream and block vital downstream blood passages.

Medical devices have been developed to attempt to deal with the problem created when debris or fragments enter the circulatory system following vessel treatment utilizing any one of the above identified procedures. One approach which has been attempted is the cutting of any debris into minute sizes which pose little chance of becoming occluded in major vessels within the patient's vasculature. However, it is often difficult to control the size of the fragments which are formed, and the potential risk of vessel occlusion still exists, making such a procedure in the carotid arteries a high risk proposition.

Other techniques include the use of catheters with a vacuum source which provides temporary suction to remove embolic debris from the bloodstream. However, as mentioned above, there can be complications associated with such systems if the catheter does not remove all of the embolic material from the bloodstream. Also, a powerful suction could cause trauma to the patient's vasculature.

Another technique which has had some success relies on a filter or trap downstream from the treatment site to capture embolic debris before it reaches the smaller blood vessels downstream. The placement of a filter in the patient's vasculature during treatment of the vascular lesion can reduce the presence of the embolic debris in the bloodstream. Such embolic filters are usually delivered in a collapsed position through the patient's vasculature and then expanded to trap the embolic debris. Some of these embolic filters are self-expanding so a restraining sheath is needed to maintain the filter in a collapsed position until it is ready to be deployed within the patient's vasculature. At the target site, the physician can retract the proximal end of the restraining sheath to expose the expandable filter thus allowing the filter to self-expand. Once the procedure is completed, the filter can be collapsed, and the filter with the trapped embolic debris can then be withdrawn from the vessel. While a filter can be effective in capturing embolic material, the filter still needs to be collapsed and removed from the vessel. During this step, there is a possibility that trapped embolic debris can backflow through the inlet opening of the filter and enter the bloodstream as the filtering system is being collapsed and removed from the patient. Therefore, it is important that any captured embolic debris remain trapped within this filter so that particles are not released back into the body vessel.

In order to properly locate and deploy an expandable filter at the target site, some prior art expandable filters vessel are affixed to the distal end of a guide wire or guide wire like member. This allows the filtering device to be steered in the patient's vasculature as the guide wire is positioned by the physician. Once the guide wire is in proper position in the vasculature, the embolic filter can be deployed to capture embolic debris. The guide wire can then be used by the physician to deliver interventional devices such as a balloon angioplasty dilatation catheter or a stent delivery catheter, and to perform the interventional procedure in the area of treatment. After the procedure is completed, a recovery sheath can be delivered over the guide wire using over-the-wire or rapid exchange (RX) techniques to collapse the expanded filter for removal from the patient's vasculature.

Some prior art filtering devices use a filter assembly that separately tracks over the guide wire and attaches to a special fitting or stop located near the distal end of the guide wire. These filtration devices require the stop to be placed near the distal end of the guide wire. The bulk and location of the stop on the guide wire, however, can detrimentally affect the ability of the physician to steer the guide wire and to reach the target area in the patient's vasculature. Depending on its shape and size, the stop formed on the guide wire might cause the guide wire to hang or catch inside a patient's tortuous anatomy, or it might injure the vessel wall. These particular filter systems also require additional manufacturing procedures to properly mount the stop onto the steerable guide wire. Accordingly, the presence of the stop near the distal end of the guide wire may cause unwanted problems during advancement of the guide wire through the patient's vasculature.

Furthermore, many physicians have a preferred brand or type of guide wire that they use during select intravascular procedures. If the filter device requires a specially designed guide wire having a unique fitting or stop to lock to that filter device, then the physician cannot use his or her preferred guide wire due to possible incompatibility between the favored guide wire and the filter device.

Therefore, what is needed is a mechanism for locking a medical device onto a conventional, unmodified guide wire. In particular, there is a need for a filtering system that includes a filter device that is easy to deliver, attaches to a standard guide wire, and eliminates the need for a special fitting or stop formed on the guide wire to help position the filter device. Also, it would be beneficial if the filtering device can be rotatably mounted on the guide wire to prevent the deployed filtering device from rotating while the guide wire is torqued and possibly scraping the vessel wall. The present invention satisfies these and other needs.

SUMMARY OF THE INVENTION

The present invention relates to a medical device, such as an embolic filter assembly, having a locking component that locks the device to a standard guide wire. As such, the locking component can be used in conjunction with conventional, off-the-shelf guide wires, and does not need specially-designed guide wires with fittings or stops to engage the locking component. Furthermore, the locking component of the present invention is capable of being attached to or formed as part of any medical device that needs to be positioned on a guide wire and locked in place.

The locking function of the present invention is intended to selectively immobilize, preferably in one or both directions, the medical device at a predetermined position along the length of the guide wire. Although linear travel may be limited proximally, distally, or both, the medical device may still be free to rotate about the guide wire even when locked to the guide wire.

In one embodiment, the embolic protection system includes a guide wire with an elongated core without a stop, a filter assembly having a proximal end and a distal end, and a locking component disposed at one of the ends of the filter assembly. The locking component is adapted to lock onto any point along the guide wire elongated core. Several embodiments of the locking component can be used to lock the filter assembly onto the guide wire, and each of these embodiments is described in detail below.

An embodiment of the locking component used for securing a filter assembly to an elongated wire core includes a frame bushing having a tapered inner diameter that is disposed on the filter assembly. The locking component also includes an interlocking bushing having a first end and a second end, wherein the second end is slidably positioned within the tapered profile, inner diameter of the frame bushing. Both the frame bushing and complementary interlocking bushing are designed to track over the elongated wire core. In this embodiment, filter assembly is secured to the elongated wire core when the second end of the interlocking bushing is pushed into the tapered inner diameter of the frame bushing. A diameter of the second end of the interlocking bushing is decreased from the force applied by the tapered inner diameter when the interlocking bushing is pushed toward and into the frame bushing, thereby causing the second end of the interlocking bushing to grasp or grip the elongated wire core. An optional third bushing, called a crush bushing, may also be used to lock onto the elongated wire core. The third bushing is disposed partially within the interlocking bushing, and as the second end of the interlocking bushing is forced into a smaller diameter, the crush bushing is deformed to constrict onto the elongated wire core.

In another embodiment, an embolic protection system includes a guide wire having an elongated core without stops, and a filter assembly which is disposed on the elongated core for movement therealong. The filter assembly has a first end and a second end, and the locking component in this embodiment is a self-contracting elastic tube disposed on one of the ends of the filter assembly. One end of the elastic tube extends from the filter assembly while a free end of the elastic tube grips down around the wire core to secure the filter assembly thereon. When delivering the filter assembly to the distal end of the guide wire inside a body lumen, a hypotube is used to help move the filter assembly along the wire core. The hypotube is preferably positioned beneath the self-contracting elastic tube to prevent the elastic tube from gripping the guide wire while the filter assembly is traveling along the wire core; as such, the free end of the elastic tube is removably mounted onto the hypotube. By slightly withdrawing the hypotube from underneath, the free end of the elastic tube at least partially self-contracts and locks down onto the wire core.

In yet another embodiment, the locking component or locking device is designed to allow free movement of the filter assembly in one direction and to prevent movement of the filter assembly in the opposite direction. For instance, the locking device is disposed at one end of the filter assembly and allows the filter assembly to move distally toward the treatment site along the guide wire, but locks and prevents the filter assembly from traveling proximally toward the physician. In this embodiment, the locking device includes a thrust bearing. The thrust bearing includes a housing having a tapered interior diametrical profile, and a roller positioned inside the housing that wedges against the guide wire when rolling along the tapered interior diametrical profile of the housing from a greater diameter to a lesser diameter.

In order to control movement in opposite directions, it is possible to have a first locking device disposed at the first end of the filter assembly and a second locking device disposed at the second end of the filter assembly, where the first locking device prevents movement of the filter assembly in the distal direction and the second locking device prevents movement of the filter assembly in the proximal direction. In order to move the filter assembly along the guide wire distally toward the treatment site, the first locking device is temporarily disabled. To temporarily disable the first locking device, a hypotube engages the roller therein to prevent the roller from moving along the tapered interior diametrical profile and wedging itself against the housing and guide wire. Once the filter assembly is in position, the hypotube is withdrawn. The wedging action is thus enabled, and the first locking device prevents the filter assembly from moving farther distally.

A further embodiment of a locking component or interlocking mechanism includes a housing containing a gripping member that has an expanded state and a contracted state. The interlocking mechanism also includes a cap that engages or screws onto an end of the housing. Once the filter assembly is located at the desired position on the guide wire, the filter assembly is locked-onto the guide wire by tightening the cap onto the housing to transform the gripping member from the expanded state to the contracted state. In one embodiment, the gripping member is a threaded collet, and the cap includes a tapered inner diameter with complementary threads. When the cap is rotationally advanced onto the collet, the action forces the collet into the contracted state thus gripping on to the guide wire.

In another embodiment the gripping member is an o-ring, and the cap having a longitudinal axis, includes an internal surface oriented perpendicularly to the longitudinal axis. As such, when the cap is screwed onto the housing, the action compresses the o-ring into the contracted state to grip the guide wire.

In still another embodiment, an embolic protection system includes a guide wire having an elongated core with a proximal end and a distal end, and a coil disposed at the distal end of the guide wire. A filter assembly has first and second ends and is disposed for travel along the guide wire core, and has a locking component. The locking component is a self-contracting locking coil extending from the filter assembly with a free end. Alternatively, the locking coil may be a discrete structure that is bonded to one of the ends of the filter assembly. The system further includes an optional hypotube disposed over the guide wire, and on which is mounted the locking coil. In use, once the filter assembly is moved to the distal end of the guide wire, the hypotube is at least partially withdrawn from underneath the free end of the locking coil. This allows the free end to contract and grip the tip coil or like structure of the guide wire.

In various other embodiments, the locking component of an embolic protection system includes a variety of shrink tubes. The shrink tube extends from one end of the embolic filter, and both track over a standard guide wire without a stop. At the deployment site, the shrink tube is thermally or chemically actuated so that it shrinks down in diameter to grip the wire core. For this to occur, the shrink tube is preferably made from a shape memory metal or polymer.

If made from a metal, the material may be a nickel-titanium alloy having an austenitic shape set to a smaller diameter while the martensitic shape is deformed to have a larger diameter to facilitate movement along the guide wire. To activate the locking function, heat is introduced to the shrink tube so that the alloy transforms from martensite to its remembered austenitic shape. This causes the shrink down in diameter. Alternatively, the shrink tube may already be in the austenitic phase while in the body lumen, and a hypotube supporting the shrink tube from underneath prevents the shrink tube from shrinking. The hypotube is withdrawn at the appropriate instance thus allowing the shrink tube to constrict onto the guide wire.

If the shrink tube is made from a polymer instead of a metal, it may be a heat shrinkable type. Such heat shrinkable materials include polytetraflouroethylene (PTFE), polyvinylchloride (PVC), polyethylene, and the like. Other shape memory polymeric materials can change by a change in acidity, water absorption, and the like. Once at the filter lockdown site, the shrink tube is exposed to heat or similar catalyst.

The present invention further provides a separately deliverable filter assembly having an expandable basket or cage and a filter element. In use, the filter assembly is designed to capture embolic debris created during the performance of a therapeutic interventional procedure or other unwanted particulates entrained in the fluid of a body vessel. The present invention allows the physician to deliver the guide wire of his or her choice with "front line" capabilities to steer through the tortuous anatomy, while still being able to provide filtering protection in the form of a separately deliverable attachment.

It is to be understood that the present invention is not limited by the embodiments described herein. To be sure, the present invention can be used in arteries, veins, and other body vessels. By altering the size of this design, the present invention would be suitable for coronary, peripheral, and neurological applications. Other features and advantages of the present invention will become more apparent from the following detailed description of the invention when taken in conjunction with the accompanying exemplary drawings.

BRIEF DESCRIPTION OF THE DRAWINGS

FIG. 3 is a side elevational view, partially in cross-section, of a standard guide wire with distal tip coil which can be used with the present invention.

FIG. 4 is a side elevational view, partially in cross-section, of a proximal end of a filter assembly including a locking component in an unlocked position on a guide wire.

FIG. 5 is a side elevational view of the filter assembly of FIG. 4 with the locking component locked onto the guide wire.

FIG. 6 is a side elevational view of the filter assembly of FIGS. 4 and 5 with the locking component locked onto the guide wire, and a clawed hypotube locked onto the locking component.

FIG. 7 is a side elevational view of the filter assembly of FIGS. 4, 5, and 6 with the clawed hypotube attached to the locking component and a recovery sheath advanced over the filter assembly.

FIG. 9 is a side elevational view, partially in cross-section, of an alternative embodiment of the guide wire locking component including an elastic tube.

FIG. 10 is a side elevational view, partially in cross-section, of another embodiment of the guide wire locking component including two roller clutch assemblies, with one attached to the proximal end of the filter assembly and the other attached to the distal end of the filter assembly.

FIG. 11 is a side elevational view, partially in cross-section, of the roller clutch assembly attached to the proximal end of the filter assembly of FIG. 10, and showing a hypotube engaging the roller to prevent the roller from locking.

FIG. 12 is a side elevational view, partially in cross-section, of the roller clutch assembly attached to the proximal end of the filter assembly of FIGS. 10 and 11, and showing the hypotube removed and the roller pinching the guide wire.

FIG. 13 is a side elevational view of another embodiment of a locking component attached to the proximal end of a filter assembly.

FIG. 13a is a side elevational view of a shape memory locking tubing attached to the proximal end of the filter assembly.

FIG. 14 is a side elevational view of another embodiment of a locking component attached to the filter assembly.

DETAILED DESCRIPTION OF THE PREFERRED EMBODIMENTS

The present invention relates to a locking component used to lock a medical device on to a standard guide wire. As such, the locking component does not need to be used with a specially designed guide wire having a complementary "fitting" or "stop" thereon in order to accomplish the locking function. That is, such a standard guide wire has no "fitting" or "stop" defined as any structure formed on the wire or attached thereto before sterilization, whose position relative to the wire is generally stationary or has very restricted linear and/or rotational movement, that is intended to engage a mating locking component of a filtering device or like medical device in order to (a) prevent or limit the movement of that filter device along the guide wire, and/or to (b) assist in the deployment of the filter device.

The above definition of a "fitting" or "stop," however, does not encompass common fixtures found on a guide wire core such as a tip coil, a shaping ribbon, or the like. Further, the definition of "fitting" or "stop" should not encompass what is known in the art as a "step catch." A "step catch" is a stop that is first tracked over the wire so that a mating component can later engage that stop.

For ease of illustration, the following exemplary embodiments are directed to locking components that are attached or disposed on embolic filtering devices, although it is understood that the present invention is applicable for use with other medical devices that can be delivered in over-the-wire fashion and locked to a standard guide wire. It is contemplated that by altering the size of the components, the present invention can be suitable for coronary, peripheral, and neurological applications. It is understood that the present invention is not limited by the embodiments described herein.

Figure 1:
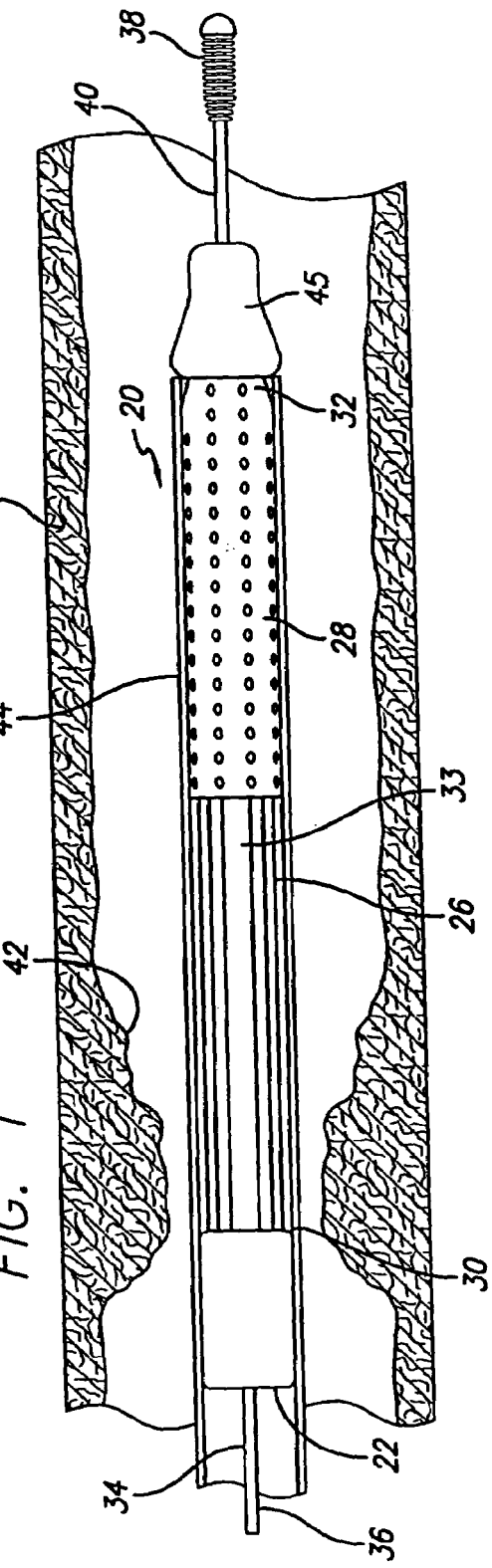
FIG. 1 is a side elevational view, partially in cross-section, of a guide wire with an embolic filter assembly in the compressed state, and a generic representation of a locking component, all positioned inside a patient's body lumen.
Figure 2:
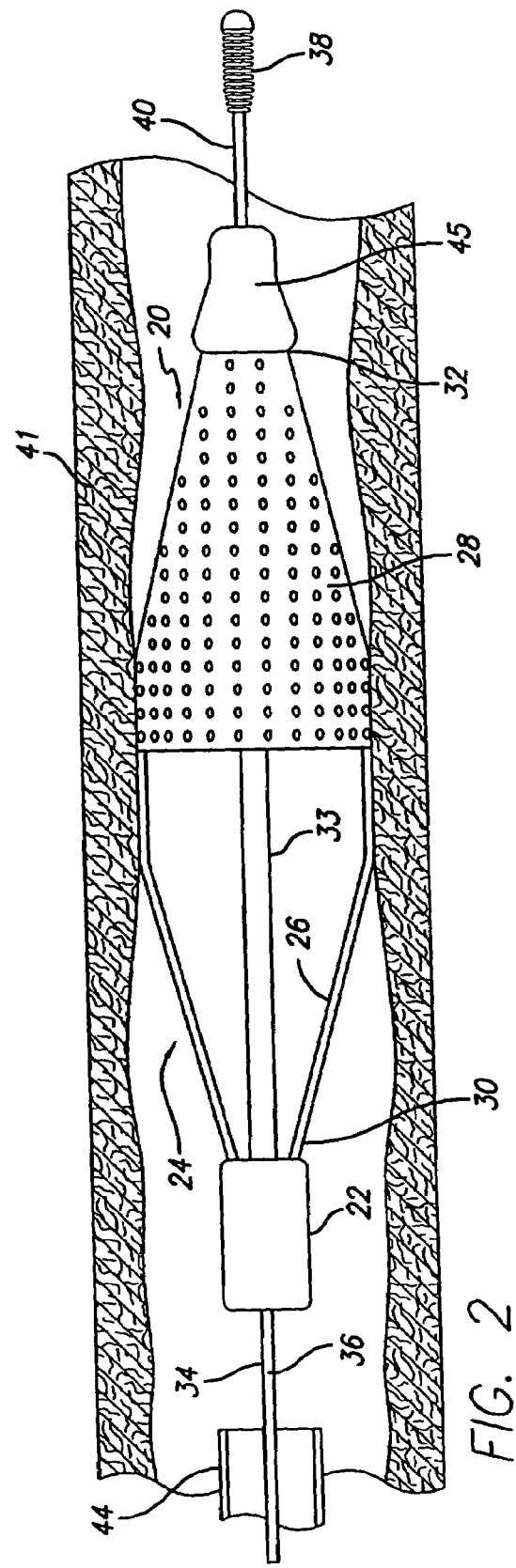
FIG. 2 is a side elevational view of the filter assembly and guide wire locking component of FIG. 1 shown deployed within the body lumen.

Turning now to the drawings, in which like reference numerals represent like or corresponding elements in the drawings, FIGS. 1 and 2 illustrate an embolic filtering system 20 that includes a guide wire locking component 22; the locking component 22 is generically represented in the drawing. The embolic filtering system 20 is designed to capture, for example, embolic debris which may be created and released into a body lumen during an interventional procedure. The embolic filtering system 20 can also be used to filter any unwanted particles entrained in the fluid of a body lumen such as large microspheres of a therapeutic agent that may be released into the lumen during a localized drug delivery procedure.

The embolic filtering system 20 preferably includes an expandable filter assembly 24 having a self-expanding basket or cage 26 and a filter element 28 attached thereto. The filter assembly 24 has a proximal or first end 30 and a distal or second end 32, and in the embodiment shown in FIG. 1, the locking component 22 is shown disposed at the proximal end 30 of the filter assembly 24. A basket hypotube or coil 33 (and sometimes referred to as an inner housing) is also shown as part of the embolic filtering system 20. The basket hypotube 33 is connected between the proximal and distal ends 30 and 32, and allows the filtering device to be engaged with an elongated (solid or hollow) cylindrical tubular shaft, such as a steerable guide wire 34 having an elongated core 36. The guide wire in the drawings is also shown to have an optional distal tip coil 38. The guide wire 34 has a proximal end section (not shown in FIGS. 1 and 2) that extends outside the patient, and a distal end section 40.

In FIGS. 1 and 2, the embolic filtering system 20 is depicted within an artery 41 or other body lumen of the patient. A portion of the artery 41 has an area that needs treatment, for example, atherosclerotic plaque or stenosis 42 that has built up against the inside wall of the artery 41. To operate the embolic filtering system 20, the physician first inserts the guide wire 34 into the vasculature of the patient, advancing and then positioning the distal end 40 of the guide wire 34 past the area of treatment or lesion. The guide wire 34 is advanced and steered by the physician using techniques well known in the medical profession.

The physician next delivers an interventional device along the guide wire to treat the stenosis 42, or he can first deploy an embolic filtering device past the stenosis 42 to catch possible particles that could break from the stenosis during treatment. If the physician decides to opt for distal embolic protection, a restraining or delivery sheath 44 that delivers the filter assembly 24 separately along the guide wire 34 in a collapsed position can be advanced along the guide wire and downstream from the lesion.

Once the filter assembly 24 is positioned at the distal end section 40 of the guide wire downstream from the lesion, it is locked against the guide wire in place. The expandable filter assembly 24 can then be deployed by the physician by simply retracting the delivery sheath 44 proximally to expose the expandable filter assembly 24. As the restraining sheath 44 is retracted, the self-expanding basket 26 immediately begins to expand within the body lumen 38, causing the filter element 28 to expand as well. By having a locking component 22 that can attach at any point along the elongated core 36 of the guide wire without the use of stops or other mechanisms specially formed on the guide wire, the physician is able to use a standard, off-the-shelf guide wire of his or her choice.

As shown in FIGS. 1 and 2, the filter assembly 24 may include an obturator 45 made from a soft material such as PEBAX 40D which provides an atraumatic tip to the filter assembly as it is advanced over the guide wire within the patient's vasculature. The soft tipped obturator 45 helps to prevent the distal end of the filter from scraping the walls of the body vessel as it is advanced therethrough. This same type of obturator can be used in accordance with any of the embodiments of the present invention filter assembly with a locking component.

Referring specifically now to FIG. 2, the embolic filtering system 20 is shown in its expanded position within the patient's artery 41. A treatment device (not shown), such as an angioplasty catheter or stent bearing catheter, can be delivered over the guide wire 34 to the area of plaque stenosis for treatment. Any embolic debris created during an interventional procedure released into the bloodstream enters the filter assembly 24 located downstream from the area of treatment. Once the procedure is completed and the embolic debris is collected in the filter element 28, the filter assembly 24 is collapsed by a recovery sheath (not shown) that slides over the filter assembly. The filter assembly 24 is now ready for removal from the patient's vasculature.

As mentioned earlier, the guide wire locking component 22 is preferably used with a conventional guide wire 34. Referring now to FIG. 3, a representation of a conventional guide wire 34 is shown. The guide wire 34 depicted in FIG. 3 includes an elongate core member 36 with a proximal section 48 and a distal section 40. A flexible body member 38 such as a helical tip coil is disposed around the distal section 40, and the helical coil 38 has a proximal end 52 and a distal end 54. In this embodiment, the helical coil 38 has a relatively constant diameter from the proximal end 52 to the distal end 54. The helical coil 36 can be attached to the guide wire 34 at the proximal end 52 by a solder or weld bead 56. Also in this embodiment, the distal end 54 has a rounded solder ball 58. In the event that the spacing between coils is too tight, i.e., the tip is too stiff and does not bend through tortuous anatomy, the physician can simply apply a small amount of proximal force to the coils to cause a portion of the tip coil to expand longitudinally, thus creating space between coil turns.

In general, the standard guide wire used in conjunction with the various embodiments of the present invention locking component does not have a stop, and none is shown in FIG. 3. To be sure, the guide wire can be a standard, off-the-shelf type with some or all of the common structures found on a guide wire, such as tip and intermediate coils, a tapered shoulder, a shaping ribbon, radiopaque markers, coatings of all varieties, solder beads, tip ball, etc. But such a standard guide wire has no "fitting" or "stop" as defined above.

Referring now to FIGS. 4-7, one particular embodiment of a guide wire locking component 22a made in accordance with the present invention is shown exemplifying the various states that the locking component 22a takes when being locked onto a conventional guide wire 34. As shown specifically in FIG. 4, the locking component 22a includes an interlocking bushing 60 having a first end 62 and a second end 64. The interlocking bushing 60 also includes a tapered exterior portion 66 and a central passage 68 extending between the first end 62 and the second end 64. There is also a ring 69 disposed at the second end 64 of the interlocking bushing 60. The locking component 22a further includes a frame bushing 70 having a first end 72 and a second end 74. A central passage 76 runs through frame bushing 70 from the first end 72 to the second end 74, and there is a tapered inner diameter section 78 located at the first end 72. There is a recess 80 formed on the inner diameter of the frame bushing adjacent to the tapered inner diameter section 78. Another recess 82 is formed on the exterior of the frame bushing 70 near the first end 72. As shown in the drawings, the second end 74 of the frame bushing 70 is attached to the proximal end 30 of the filter assembly 24, through mechanical engagement, chemical bonding, or any other method that is known in the art. In an alternative embodiment, the frame bushing 70 can be formed as part of or integral with the filter assembly 24 structure.

The second end 64 of the interlocking bushing 60 is fitted within the central passage 76 of the frame bushing 70 at the first end 72 and is secured inside the central passage 76 of the frame bushing 70 by a lip 84 formed at an opening on the first end 72 of the frame bushing. In a preferred embodiment, the locking component 22a further includes a crush bushing 86 that is disposed within the central passageways 68 and 76 of both the interlocking bushing 60 and frame bushing 70. As seen in the drawings, the length of the crush bushing 86 preferably extends from near the first end 62 of the interlocking bushing 60 to the recess 80 formed inside the frame bushing 70, although the length may vary.

In use, the embolic filtering system 20 including locking component 22a, is positioned at the distal end section 40 of the pre-deployed guide wire 34 by advancing the delivery sheath 44 and a floating hypotube 88 together distally. As shown in FIG. 4, the floating hypotube 88 is disposed between the guide wire 34 and the delivery sheath 44, wherein a distal end 90 of the floating hypotube abuts the first end 62 of the interlocking bushing 60 and helps move the filter assembly 24 along the guide wire 34. Once the filter assembly 24 is in a desired position along the guide wire 34, the filter assembly 24 can be locked into place by pushing the floating hypotube 88 in a distal direction while the filter assembly 24 is still in a collapsed state inside the delivery sheath 44. As the floating hypotube 88 is pushed distally, the delivery sheath 44 holds the filter assembly 24 in position on the guide wire, and the interlocking bushing 60 is pushed toward and into the frame bushing 70. The second end 64 of the interlocking bushing 60 is pushed along the tapered inner diameter section 78 of the frame bushing 70, and as the inner diameter along the tapered inner diameter section 78 narrows, the outer diameter of the second end 64 of the interlocking bushing also narrows, thereby deforming the crush bushing 86 and securing the filter assembly 24 onto the guide wire 34. In an embodiment not including the crush bushing 86, the second end 64 of the interlocking bushing would narrow to a small enough diameter to grip the guide wire and to secure the filter assembly onto the guide wire.

Referring to FIG. 5, the interlocking bushing 60 is shown snapped together with the frame bushing 70 and the crush bushing 86 gripping the guide wire. When the interlocking bushing 60 is snapped together with the frame bushing 70, they are locked together because the ring 69 is held inside the recess 80 of the frame bushing. Once the filter assembly 24 is secured to the guide wire 34, the delivery sheath is removed to allow the filter element 28 to deploy within the lumen. The floating hypotube 88 is also removed from the body lumen using conventional, over-the-wire techniques or in a rapid exchange manner if the hypotube has an open slit spanning its length.

When the intravascular procedure is completed, a recovery sheath 92, as shown in FIGS. 6 and 7, is used to collapse and remove the filter assembly 24 from the body lumen. To ensure that the filter assembly 24 does not slide distally when the recovery sheath 92 is advanced over the filter assembly, an optional clawed hypotube 94 having a clawed end 96 may be used to lock on to the locking component 22a. The clawed hypotube 94 is advanced along the guide wire 34 until the clawed end 96 reaches the first end 62 of the interlocking bushing 60. At this point the clawed hypotube 94 is further advanced, riding up the tapered exterior portion 66 of the interlocking bushing 60 and then locking into the recess 82 formed on the exterior of the frame bushing 70 as shown in FIG. 7. A physician would hold the clawed hypotube 94 in place while collapsing the filter assembly 24 with the recovery sheath 92. Once the filter assembly is retracted into the recovery sheath, the guide wire, clawed hypotube, and recovery sheath encapsulating the filter assembly are simultaneously removed from the body lumen.

Figure 8A:
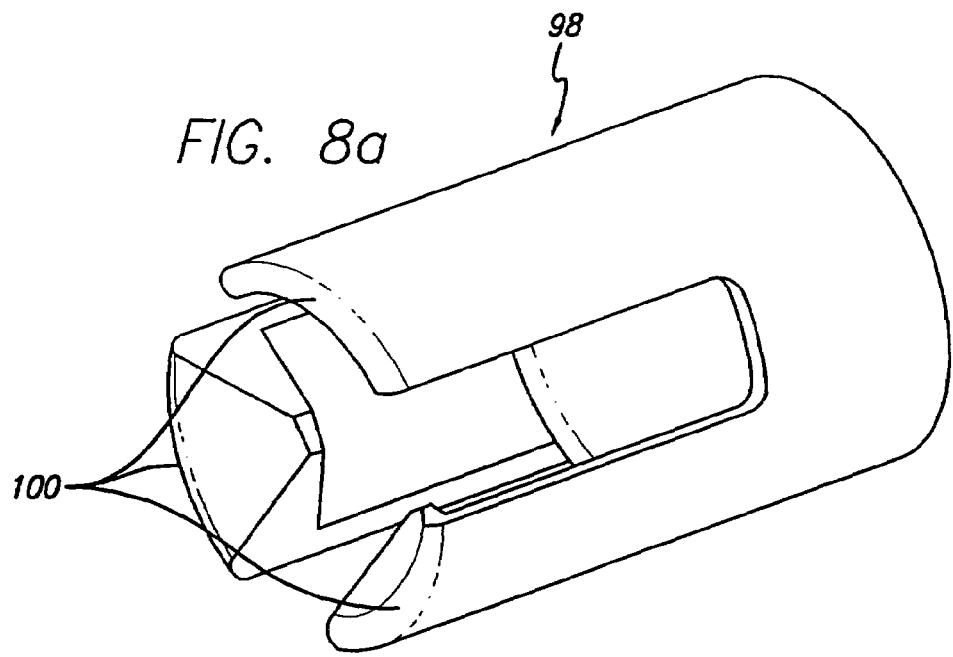
FIGS. 8*a* and 8*b* are perspective views of embodiments of a claw component that can be connected to the clawed hypotube.
Figure 8B:
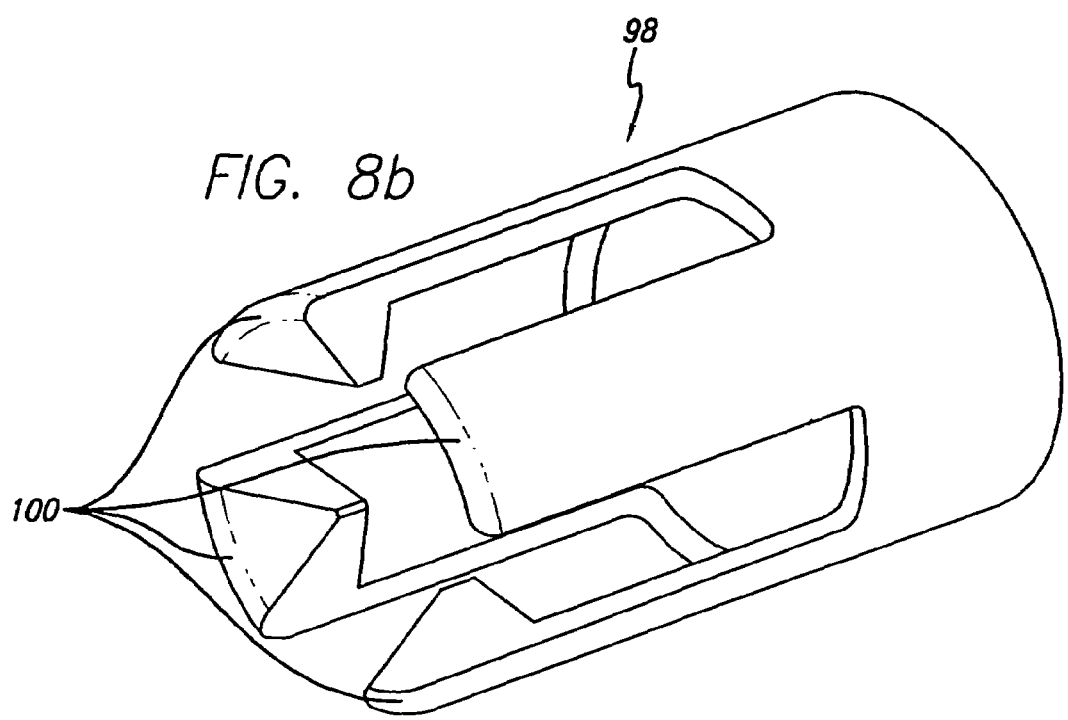

In another embodiment shown in FIGS. 8a and 8b, the clawed end of the clawed hypotube can be made as an additional claw component 98 having legs 100 that is connected in some way to or extends from the clawed hypotube. The additional claw component 98 can vary in the number of legs, leg shape, thickness and length to minimize the locking force. FIG. 8a shows one embodiment where the claw component 98 has three legs 100, and FIG. 8b shows an embodiment where the claw component 98 has four legs.

Yet another embodiment of a locking component is shown in FIG. 9, and is designated 22b. The locking component 22b includes a bushing 102 with a central passageway 103 and a self-contracting elastic tube 104 having a free end 105 for gripping the guide wire 34. The elastic tube 104 can be made preferably from any elastomer or elastic polymer. The bushing 102 shown in FIG. 9 resembles the structure of the interlocking bushing 60 and frame bushing 70 when snapped together, and includes a first end 106, a second end 108, a tapered exterior portion 110 on the first end, and a recess 112 that is located adjacent to the tapered exterior portion. Also included in this locking component 22b is an inner housing tube 114 that is disposed within the central passageway 103 of the bushing 102, and the inner housing tube has a connecting end 116 that extends proximally outward from the first end 106 of the bushing 102. Although not shown in the drawings, the inner housing tube 114 may extend to the distal end 32 of the filter assembly 24. In other embodiments, the inner housing tube 114 can be a coil.

In this embodiment, the second end 108 of the bushing 102 is optionally bonded to the proximal end 30 of the filter assembly 24 and to the outer diameter of the inner housing tube 114. There is also an optional bond between the outer diameter of the connecting end 116 of the inner housing tube 114 and the inner diameter of a portion of the elastic tube 104. Of course, these structures may alternatively be formed as one piece with the filter assembly 24.

To prevent the free end 105 of the elastic tube 104 from contracting and gripping onto the guide wire 34 during delivery of the filter assembly 24 to the distal end section 40 of the guide wire, a floating hypotube 118 is positioned underneath the elastic tube 104 and abuts the connecting end 116 of the inner housing tube 114. The free end 105 of the elastic tube 104 is stretched to fit over the floating hypotube 118. There may be a lubricious coating on the contacting surfaces of housing tube 114 and floating hypotube 118 to minimize friction. This design allows the floating hypotube 118 to push directly against the inner housing tube 114 for basket deployment.

Once the filter assembly 24 including the locking component 22b is positioned at the distal end section 40 of the guide wire, the floating hypotube 118 is translated proximally while the delivery sheath 44 is held stationary. The hypotube 118 optionally has a length sufficient long for the physician to access and move it from its proximal end; a linkage of some type can be used for this purpose too. The movement of the floating hypotube 118 relative to the elastic tube 104 at least partially dismounts the free end 105 of the elastic tube 104 from the floating hypotube 118. When dismounted from the floating hypotube 118, the free end 105 of the elastic tube 104 constricts and grips onto the guide wire 34 to secure the filter assembly 24 thereon. This embodiment of the filter assembly 24 shown in FIG. 9 can be removed from the body lumen in a similar manner as the embodiment having locking component 22a shown in FIGS. 6 and 7 by using the clawed hypotube 94 to lock into the recess 112 of the bushing 102.

Although a particular embodiment is shown in FIG. 9, it is contemplated that the locking component 22b could include only the elastic tube 104 without the bushing 102, and the inner housing tube 114 could be attached only to the proximal end of the filter assembly 24. Also, it is contemplated that the elastic tube 104 can be attached directly to or formed as part of the proximal end of the filter assembly 24 without the need for the inner housing tube 114 on the bushing 102. One advantage of using the elastic tube 104 is that it can withstand high axial forces that may be encountered during delivery of the filter assembly 24.

Another embodiment of the present invention is illustrated in FIGS. 10-12. This embodiment also allows a filter assembly 24 to be positioned and locked on a pre-deployed, standard guide wire 34 that does not include any stops. Referring to FIG. 10, the embolic filtering system 20 is shown on a guide wire optionally having two locking components or devices 22c attached to or formed as part of both the proximal end 30 and the distal end 32 of the filter assembly 24. The locking device 22c allows free movement of the filter assembly in one direction and prevents movement of the filter assembly in the opposite direction. The locking device 22c on the proximal end 30 of the filter assembly in FIG. 10 prevents movement in the distal direction while the locking device 22c on the distal end 32 of the filter assembly is attached to prevent movement in the proximal direction, thereby positionally affixing the filter assembly along the length of the guide wire.

The locking device 22c of this embodiment is a thrust bearing. The thrust bearing includes a housing 120 having a first end 122 and a second end 124, with a tapered profile interior diametrical section 126 adjacent to the first end and a flat profile interior diametrical section 128 adjacent to the second end. Located within the housing 120 is a roller 130 that wedges against the guide wire when the roller rolls along the tapered interior diameter of the housing from a greater diameter to a lesser diameter. The roller 130 in this embodiment includes a thrust plate 132 that holds a loose set of ball, pin, or needle bearings 134 in a circular arrangement. An optional spring 136 is positioned inside the housing 120 within the flat interior diameter section 128 and one end of the spring is pressed against the thrust plate 132 to bias the roller tightly against the tapered interior diametrical section 126. The housing 120 is hollow with openings at both ends to allow the guide wire to pass through.

When the guide wire 34 is moved in the direction away from the ramp or tapered interior section 126, the guide wire passes with little resistance. On the other hand, when the guide wire 34 is moved in the direction of the tapered interior section 126, the biasing force from the spring 136 urges the roller 130 onto the tapered interior section. The smaller space of the tapered interior section forces the ball bearings closer together and reduces the inside diameter of the roller thereby wedging or pinching the roller down onto the guide wire. Accordingly, this roller clutch mechanism is self-actualizing and relies on a wedging principle of operation.

In FIG. 10, the second end 124 of the housing 120 is attached to or extends from the proximal end 30 of the filter assembly 24, and on the distal end 32 of the filter assembly, the second end 124 of another housing 120 is attached or extends therefrom. The locking component 22c at the ends of the filter assembly 24 are mirror images of one another. Since the locking component 22c on the proximal end 30 of the filter assembly 24 prevents movement distally, the locking component needs to be disabled while the filter assembly travels along the guide wire toward the distal end section 40. To accomplish this, an optional floating hypotube 138 (shown in FIG. 11) tracks over the guide wire 34 and is situated against the locking component 22c at an opening at the first end 122 of the housing 120. The floating hypotube 138 is attached to or is formed from the proximal end 30 of the filter assembly 24.

Referring again to FIG. 11, during delivery of the filter assembly, a distal end 140 of the floating hypotube 138 is positioned against the thrust plate 132 to keep the roller 130 off of the tapered interior section thereby preventing the wedging action. The filter assembly can then be delivered to the treatment area in a similar manner as previously discussed, with the exception that a floating hypotube 138 is used to disable the locking component 22c on the proximal end 30 of the filter assembly to enable free movement distally. Once the filter assembly 24 is in position on the guide wire 34, the floating hypotube 138 disengages from the housing 120, as shown in FIG. 12, to prevent further distal movement of the filter assembly. As shown in the drawing, the locking component 22c at the distal end 32 of the filter assembly is already activated to prevent proximal movement. Consequently, the filter assembly 24 is secured in both directions on the guide wire.

FIG. 12 shows the roller 130 clamping down on the guide wire 34, preventing distal movement. The delivery sheath can then be withdrawn to allow the filter element to expand in the body lumen. When the procedure is complete, a delivery sheath is used to collapse the expanded filter assembly and to remove the filter assembly along with the guide wire from the body lumen.

Another embodiment of a locking component is shown in FIG. 13, in which shape memory is used to lock a filter assembly onto the elongated core of any guide wire with no special features such as stops to accomplish the locking function. The locking component in this embodiment is labeled 22d, and is a shape memory tubing 150 that can be attached to or formed at the proximal end 30 or the distal end 32 of the filter assembly 24. It is contemplated that one shape memory tubing 150 can be disposed at the proximal end 30, and another shape memory tubing can be disposed at the distal end 32. As shown in FIG. 13, the filter assembly 24 can have a rotatable ferrule or bushing 152 disposed at one or both of its ends to allow free rotation of the basket or filter assembly on the guide wire, and with this design, the shape memory tubing 150 can be attached to or formed as part of the ferrule or bushing.

The shape memory tubing 150 includes a tubular body 154 having a first end 156 and a second end 158. The tubular body 154 is slidably positioned along the elongated core of a guide wire, and the first end 156 is attached to or formed from the filter assembly that is to be locked to the elongated core. The second end 158 grips the elongated core when the tubular body is transformed from an expanded state to a contracted state. In an expanded state or non-contracted shape, the inside diameter of the tubular body 154 is larger than the outside diameter of the guide wire, and the tubular body 154 can be moved along the guide wire until the filter assembly is at a desired target site. At this moment, the shape memory tubing 150 transforms into the contracted state, thereby decreasing its inside diameter so that the shape memory tubing grips onto the elongated core.

In one embodiment, the shape memory tubing 150 can be made of a shape memory polymeric material such as a heat shrinkable polymeric tubing section. The tubing has an inside diameter slightly larger than the largest outside diameter of the guide wire 34 so that the filter assembly can freely traverse along the length of the guide wire. Once the filter assembly is at the desired location, the shape memory tubing is heat shrunk to its contracted state to grip onto the guide wire. The heat shrink tubing can be contracted down to grip on to the wire core, or on to any conventional structure found on a standard guide wire, such as a tip or intermediate coil, a solder bead, or the like.

To activate the polymeric heat shrink tubing material, an infrared radiation source such as a laser or focused lamp, a sterile heat gun, an injection of heated saline, or any other source of heat known in the art may be used; known methods of cross-linking thermoplastic polymer tubing may likewise be used. Indeed, all heat shrinkable, biocompatible, polymeric tubing known in the art can be used, and preferably include polynorbornene, polytetrafluoroethylene ("PTFE"), polyethylene, polyurethane, or polyvinyl chloride ("PVC").

Other shape memory polymeric materials can also be used to form the shape memory tubing 150. For example, shape memory polymers whose shape memory is triggered by means of pH or acidity change in the ambient fluid, or liquid absorption, are contemplated. Such polymeric materials can be found in, for example, U.S. Pat. No. 5,163,952 (Froix) whose contents are hereby incorporated by reference.

The shape memory tubing 150 may also include a two-component shape memory polymer, with one component being a "hard," high glass temperature polymer for setting the original shape, and the other complementary component being a "switch" low glass temperature polymer for changing the shape. These shape memory polymers can be returned to a remembered state using a number of stimuli including heat or UV light.

When applying shape memory polymers to a locking component, the filter assembly is preferably first secured onto the distal end of the guide wire while outside of the patient's body. As a result, use of these shape memory polymers as locking components can quickly transform any standard guide wire without a stop into a guide wire with an appended embolic filter. Once the filter assembly is attached to the physician's choice of guide wires, the modified guide wire with the filter assembly collapsed by a delivery sheath is inserted into and positioned within the body lumen of the patient.

In another embodiment, the shape memory tubing 150 is preferably made from a shape memory metal such as nickel-titanium ("nitinol"). FIG. 13a shows the metallic shape memory tubing 150 disposed at one end of a filter assembly. As seen in the drawing, the tubing 150 may have laser cut openings to create a strut pattern as in a stent. Strut patterns with openings having a variety of geometric shapes, sizes, and arrangements are contemplated. Although nickel-titanium is the preferred shape memory alloy to use for the shape memory tubing 150, other shape memory alloys known in the art can be used as well, including copper-aluminum-nickel, copper-zinc-aluminum, and iron-manganese-silicon alloys. Nickel-titanium with the addition of a ternary element can also be used.

The locking component embodied in the nickel-titanium shape memory alloy tubing can be attached to the guide wire before or during the medical procedure on a pre-deployed guide wire. To attach the locking component on a guide wire prior to the medical procedure, the nickel-titanium shape memory alloy tubing is heated from a low temperature, martensitic phase to a high temperature, austenitic phase, which austenitic phase recovers the remembered shape. Generally speaking, a transition temperature (usually designated $M_s$, $M_f$, $A_s$, or $A_f$) separates one phase from the other, and in one embodiment, the transition temperature is set at about 37 degrees C., or human body temperature, or just below that temperature. When the nickel-titanium alloy is heated to above the transformation temperature, the tubing reverts to its austenitic, remembered shape. If the remembered shape is heat set to have a small diameter, reversion of the tubing to this small diameter remembered shape contracts the tubing onto the guide wire.

While below the transition temperature in the martensitic phase, the locking component with filter assembly attached is deformed to a larger diameter to fit on to the distal end of the guide wire. The locking component is then heated to above the transition temperature. It now transitions into the austenitic phase shrinking down in diameter to lock on to the guide wire. The guide wire can thus be modified to add a filter assembly to the distal tip while outside the patient's body prior to the procedure. A delivery sheath, used to collapse the self-expanding filter assembly would, of course, be needed prior to insertion in a patient.

The above principle can be applied to the shape memory tubing while inside the body. First, the shape memory tubing is joined to or is formed from one end of the filter assembly as shown in FIG. 13a. The tubing 150 is in its low temperature, martensitic phase with a large diameter to enable movement along the guide wire. Second, the filter assembly is delivered to the target site, tracking along the guide wire in a delivery sheath while the nickel-titanium shape memory tubing is thermally isolated to remain in the martensitic phase and in an expanded state until the delivery sheath is removed to deploy the filter assembly. Third, once exposed to the warmer ambient environment, the nickel-titanium shape memory tubing 150 reaches or exceeds the transition temperature at which moment the tubing 150 returns to its austenitic, remembered shape. The smaller diameter of the remembered shape contracts and clamps the tubing 150 onto the guide wire 34. The filter assembly is thus locked in place on the guide wire.

In an alternative embodiment (not shown), a hypotube is slidably disposed over the guide wire and located underneath the shape memory tubing 150. The tendency of the nickel-titanium alloy when exposed to high temperatures to revert back to its small diameter remembered shape is resisted by the fixed diameter hypotube underneath. When situated on the hypotube, the alloy is in its stress-induced martensitic (SIM) phase. Once at the target site, the hypotube is withdrawn through conventional methods thus allowing the now unsupported shape memory tubing to self-contract onto the guide wire. In the self-contraction, the alloy generally transforms from SIM to the austenitic phase. This embodiment may be more accurately characterized as applying psuedoelasticity or superelasticity of the alloy rather than the shape memory effect, because when the support or stress is removed causes the phase change, and that phase change occurs isothermally. Also, an optional lubricious coating may be added to the hypotube exterior to ease dismount of the shape memory tubing 150 from the hypotube.

The recovery or transition temperature of the nickel-titanium alloy may be altered by making minor variations in the composition of the metal and in processing the material. In developing the correct composition, biological temperature compatibility must be determined in order to select the correct transition temperature. In other words, when the nitinol metal is heated, it must not be so hot that it is incompatible with the surrounding body tissue.

Other shape memory materials may also be used, such as, but not limited to, irradiated memory polymers such as autocrosslinkable high density polyethylene (HDPEX). Shape memory alloys are known in the art and are discussed in, for example, "Shape Memory Alloys," Scientific American, Vol. 281, pp. 74-82 (November 1979), whose contents are incorporated herein by reference.

Referring now to FIGS. 14-17, another embodiment of a locking component 22e is shown, with one locking component attached to each end of the filter assembly 24. The locking component 22e or interlocking mechanism can be attached to at least one of the ends of the filter assembly and includes a housing 160 and a gripping member 162 inside the housing having an expanded state and a contracted state, and a cap 164 that engages the housing. By engaging the cap 164 with the housing 160, the gripping member 162 is transformed from the expanded state to the contracted state thereby locking the filter assembly 24 to the guide wire.

Figure 15:
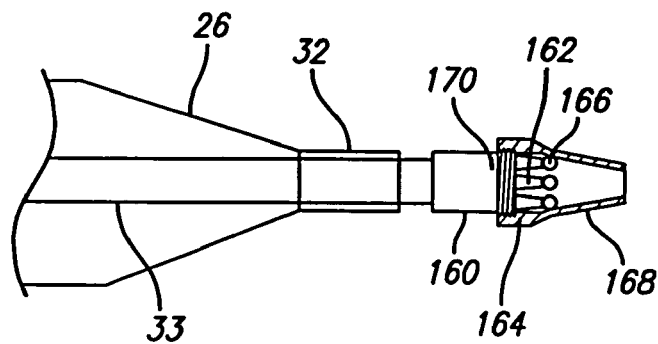
FIG. 15 is a side elevational view, partially in cross-section, of a collet-type locking component.

As seen in FIG. 15, the gripping member 162 in this embodiment refers to a collet mechanism 166. The collet mechanism 166 features a cap 164 with a tapered inside diameter 168 that engages fingers, claws, projections, or a notched lip extending from the housing 160. As the cap 164 is advanced over external threads 170, the fingers, claws, projections, or notched lip is forced to slide along the ever-decreasing inside diameter of the cap 164. As a result, the fingers, claws, projections, or notched lip is forced radially inward to clamp down on the guide wire.

Figure 16:
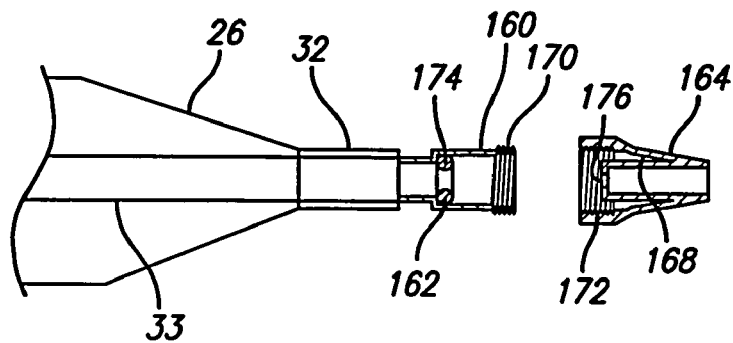
FIG. 16 is a side elevational view, partially in cross-section, of a collet-type locking component with an o-ring.

In another embodiment shown in FIG. 16, the gripping member 162 is a pliable o-ring 174 preferably made of an elastomer or soft polymer. The o-ring 174 as the name implies has a donut hole in the center, and is seated at one end within the guide wire lumen of the tubular housing 160. If the o-ring 174 is compressed to reduce its volume, the o-ring will correspondingly expand in a direction that is unrestricted to maintain that volume. A cap 164 has a compression surface 176 for engaging the o-ring 174. When a cap 164 having internal threads 172 is advanced over external threads 170 of the housing 160, the compression surface 176 engages and compresses the o-ring against the back side of the lumen, and the inside diameter of the guide wire lumen restricts expansion of the o-ring radially outward.

Because it is restricted from expansion in all other directions, to maintain its volume under this compression, the only unrestricted direction is radially inward to close down the donut hole. Thus, advancing the cap 164 compresses the o-ring which in turn closes down the donut hole thereby clamping down on a guide wire passing therethrough.

Figure 17:
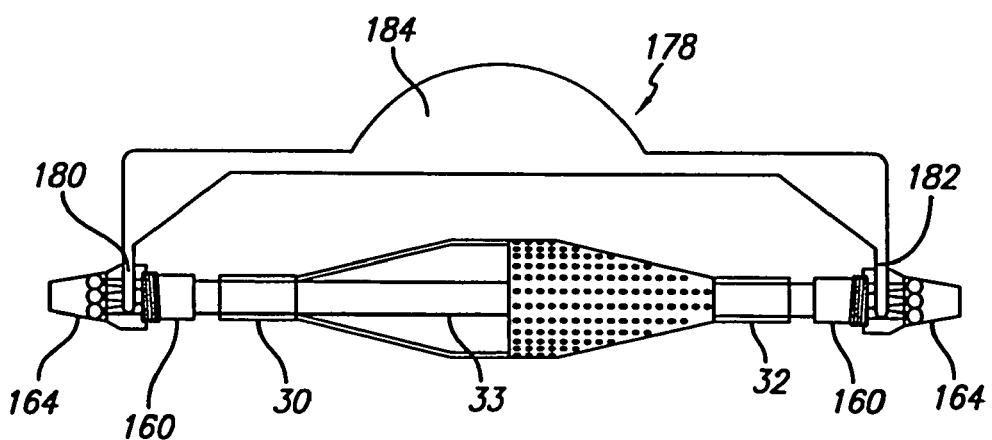
FIG. 17 is a side elevational view of a hand tool for locking the locking component of FIG. 14 attached to the caps of the locking components.

FIG. 17 shows an optional tool 178 having a first gripping end 180, a second gripping end 182, and a handle 184. The tool 178 can be used to grip the caps 164 on each of the locking components 22e found on both ends of the filter assembly 24 to screw the caps onto the housings. To operate, the filter assembly 24 including the locking components 22e is tracked over the guide wire 34 to a desired location.

Once at the desired location on the guide wire 34, the ends 180 and 182 of the tool 178 are fitted over the caps 164, which are loosely attached to the housing 160. The physician can then turn the tool 178 in one direction using the handle 184 to tighten the caps 164. Only one direction is needed to tighten both caps at once by having a left-hand thread on the locking component 22e at the proximal end 30 of the filter assembly 24 and a right-hand thread on the locking component at the distal end 32 of the filter assembly. By tightening the cap 164 onto the housing 160, the gripping member 162 is forced into its contracted state to grip onto the guide wire 34. Any standard guide wire can be transformed into a filter guide wire by attaching a filter assembly having the locking component 22e attached at one or both of its ends.

Figure 18:
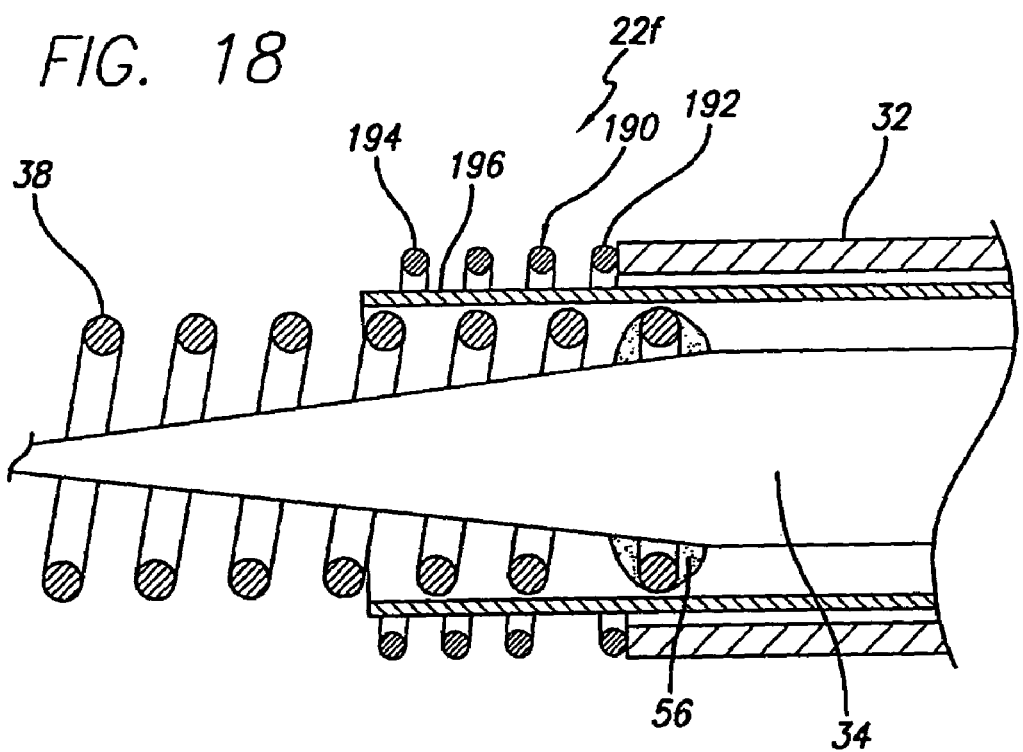
FIG. 18 is a side elevational view, partially in cross-section, of a locking coil in an expanded state positioned overlying a distal tip coil of a guide wire.
Figure 19:
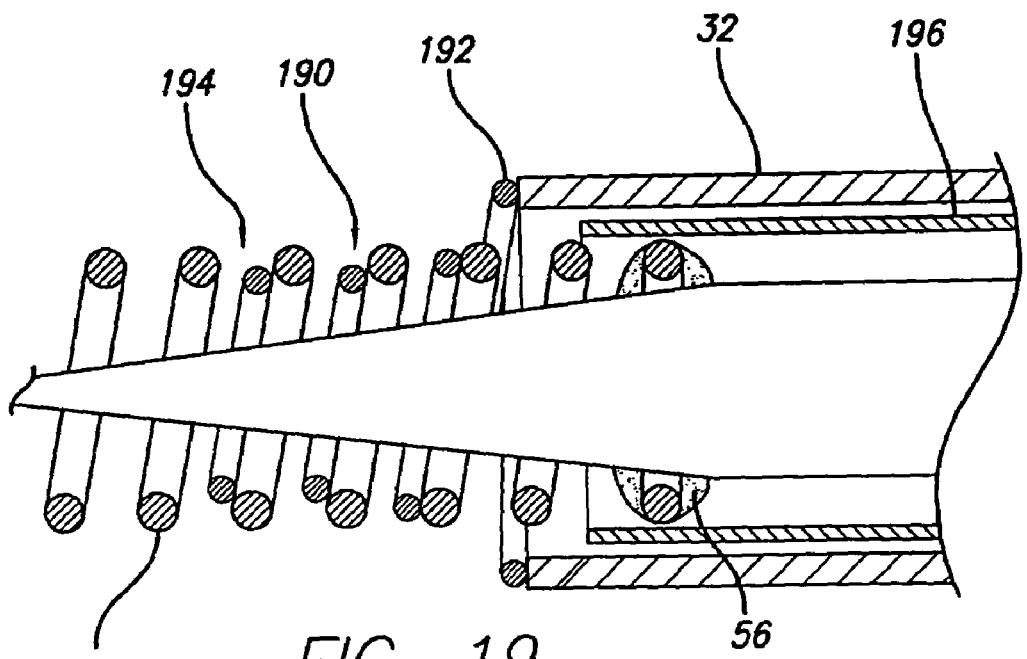
FIG. 19 is a side elevational view, partially in cross-section, of the locking coil of FIG. 18, wherein the locking coil has contracted onto the distal tip coil of the guide wire.

Referring now to FIGS. 18 and 19, a locking component is shown that can attach to any pre-deployed guide wire having a conventional distal tip and/or intermediate coil. In this embodiment, a locking component 22f is a self-contracting locking coil 190 having an attached end 192 and a free end 194, with the attached end secured to or formed as part of the distal end 32 of the filter assembly 24. The locking coil 190 is preferably made from nitinol, although other biocompatible materials may be used.

As seen in FIG. 18, an optional hypotube 196, preferably a thin-walled, lased hypotube, is positioned underneath the locking coil 190 and supports the free end 194 of the locking component 22f thereon. The hypotube 196 is located coaxially in between the guide wire and the filter assembly 24, and keeps the coil 190 in an expanded state while the filter assembly is moved along the guide wire to the distal end section 40. Once the hypotube 196 is at least partially or entirely withdrawn, the support for the locking coil 190 is partially or totally eliminated. As a result, the free end 194 of the coil 190 contracts around, on top of, and/or in between the turns of the distal tip and/or intermediate coils 38.

This embodiment only requires that the guide wire have a conventional coil 38 disposed thereon, and does not require the guide wire to have any special features, such as a stop, to facilitate locking the filter assembly thereto. In this embodiment of the invention, the elongated guide wire core has no stops thereon. Further, the tip/intermediate coils 38 and locking coil 190 can have any pitch and any number of turns. The number of turns and pitches of the coils 38, 190 may be different as shown or may be the same. The wire diameters of the coils 38, 190 may be different as shown or the same. Regarding the compliance or stiffness of the coils 38, 190, this characteristic can be selected as necessary to maximize guide wire performance so long as there is enough stiffness to interlock the coils and minimize inadvertent detachment of or slippage between the coils 38, 190.

Preferably, the locking coil 190 has a smaller diameter than the tip/intermediate coils 38 to favor the interlacing action where the smaller diameter wires easily slip in between the turns of the larger tip/intermediate coils 38. Also, it is preferable to have different pitches between the locking coil 190 and the tip/intermediate coils 38 to improve contact and make for a better lock between the parts.

The locking component 22f described above can be used to attach an embolic protection device to a guide wire to capture embolic debris released into a blood vessel of a patient. A guide wire 34 having an elongated core 36 with proximal and distal ends and a coil 38 disposed at the distal end of the guide wire is inserted into a blood vessel and advanced to a treatment area. The filter assembly 24 is then slidably mounted onto the guide wire and advanced along with the hypotube 196 that is positioned between the guide wire and the filter assembly and which radially supports the self-contracting locking coil 190 in an expanded state.

The filter assembly 24, being collapsed by a delivery sheath, and the hypotube 196 are then directed to the distal end section of the guide wire which should be positioned downstream from the treatment area. Once the locking coil 190 extending from the distal end 32 of the filter assembly 24 is positioned at least partially over one of the tip coils 38 of the guide wire, the hypotube 196 is withdrawn proximally out of the body lumen, thereby allowing the free end 194 of the coil 190 to contract around the tip coil. This locks the filter assembly to the guide wire as shown in FIG. 19. The delivery sheath is then removed to allow the filter element to expand inside the body lumen.

Figure 20:
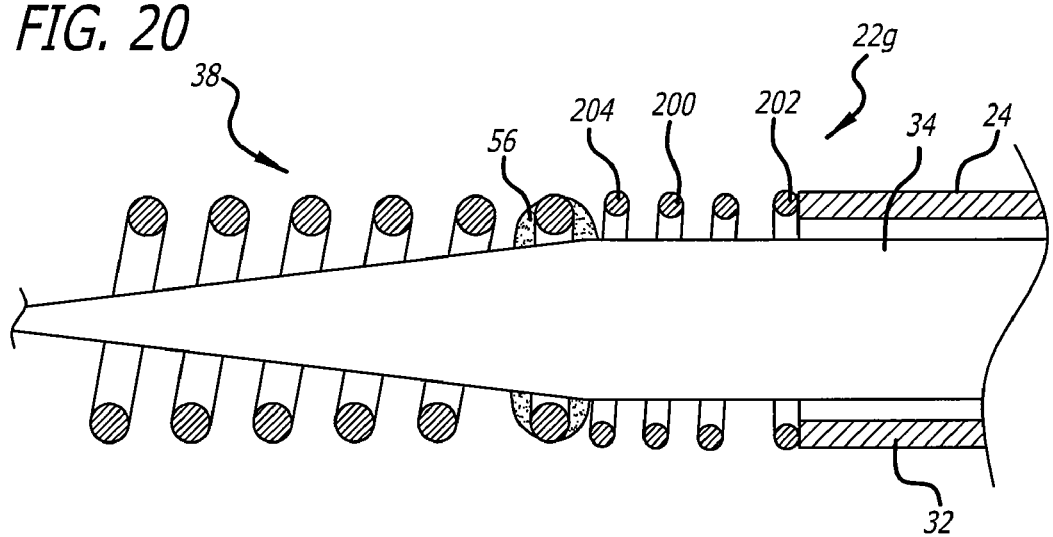
FIG. 20 is a side elevational view, partially in cross-section, of a locking coil positioned adjacent a weld bead of a distal tip coil of the guide wire.
Figure 21:
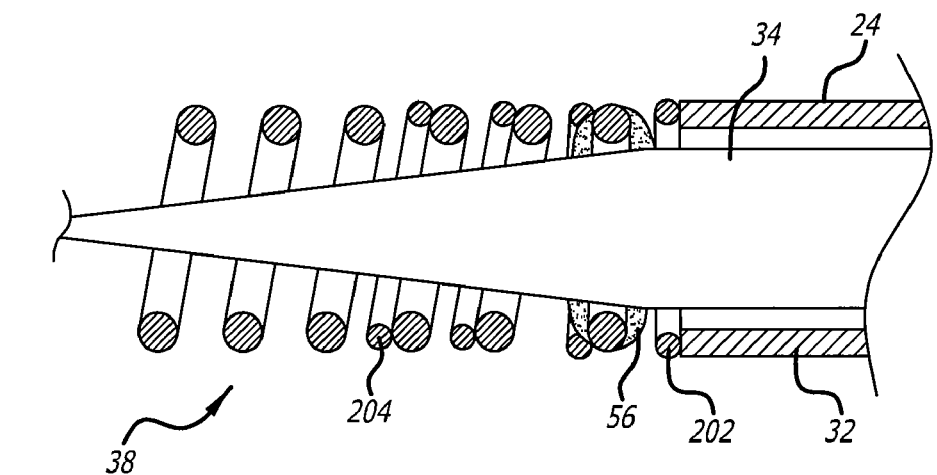
FIG. 21 is a side elevational view, partially in cross-section, of the locking coil of FIG. 20, wherein the locking coil has passed over and locked onto the weld bead and the distal tip coil.

A similar embodiment is shown in FIGS. 20 and 21, where a locking component 22g is a self-contracting locking coil 200 that is attached to or extends from the distal end 32 of the filter assembly 24 and has an attached end 202 and a securing end 204. The locking coil 200 has an inside diameter that is slightly larger than outside diameter of the elongated core of the guide wire, but slightly less than the outside diameter of a proximal solder or weld bead 206 that joins the distal tip coil 28 to the guide wire core. In this embodiment, the locking coil 200 slides up and over a bump or taper created by the solder or weld bead 56, which is one example of a protrusion, and locks into the distal tip coils 38 as shown in FIG. 21. As seen in FIG. 21, the locking coil at least partially overlies the distal coil such that turns of the locking coils and the distal coil interlace and engage with one another to lock the distal coil to the locking coil. Once the locking coil 200 is locked into the distal tip coil or coils 38, the delivery sheath can be removed to expand the filter element.

It is also possible for the locking coil 200 to be pushed over a solder that is attaching an intermediate coil to the guide wire and locked onto the intermediate coil. Hence, the locking coil 200 can be locked onto the turns of the distal coil or coils, the weld or solder bead, or both. In sum, this embodiment may be used on any guide wire having a conventional coil that is welded or soldered to the core, and no special feature such as a stop is needed to lock the locking component to the wire core.

The dimensions and specifications of each of the locking components described above can be varied to meet almost any design criteria. For coronary and other procedures which typically use about a 0.014 inch diameter guide wire, the maximum coil outer diameter should be about 0.0138 inch. The proximal guide wire core would be about 0.012 inch or the maximum diameter that would fit into the tapered opening. It should be appreciated that modifications can be made to the guide wire, filter assembly and guide wire locking component without departing from the spirit and scope of the present invention.

The elongated core which forms part of the guide wire is typically comprised of metal, preferably stainless steel or a nickel-titanium alloy or a combination thereof, but can also consist of any material that yields the approximate mechanical properties of the named metals so long as the material is sufficiently biocompatible. Other materials such as high strength alloys may also be used for the core, either alone, or in combination with other materials such as those previously mentioned. The proximal section of the core and any portion of the core not covered by the flexible body or coil may optionally be used with a lubricious coating such as a flouropolymer, e.g., TEFLON® by DuPont. It may also be coated with a silicone based coating, such as MICROGLIDE® coating used by the present assignee, Advanced Cardiovascular Systems, Inc. on many of its commercially available guide wires. Other similar coatings, for example, hydrophyllic coatings, or a combination of any of the above-mentioned coatings may also be used.

The flexible body or coil 38 can be disposed around all or part of the guide wire 34. The flexible body can be comprised of many suitable materials that allow for increasing the diameter of the guide wire in the distal section without adding substantial stiffness to that section. Suitable materials include polymers, composites, and metals. Preferably the flexible body is comprised of a helical shaped metallic coil, more preferably a metal or composition of metal or alloys with some degree of radiopacity in order to facilitate flouroscopic viewing of the device while in use. Metals suitable for the flexible body may include gold, platinum, tantalum, stainless steel, and nickel-titanium alloys, MP35N, or a combination or alloy of any of the foregoing. A flexible body comprised of metallic helical coils is typically comprised of coil winding material that can have a cross-sectional diameter of about 0.001 inch (0.025 mm) to about 0.008 inch (0.20 mm), preferably about 0.002 inch (0.05 mm) to about 0.004 inch (0.1 mm).

The expandable basket of the filter assembly can be made in many ways. One particular method of making the basket is to cut a tubular member, such as nickel-titanium hypotube, to remove portions of the tubing in the desired pattern for each strut, leaving relatively untouched the portions of the tubing which form the structure. The tubing may be cut into the desired pattern by means of a numerical or computer controlled laser. The tubing used to make the basket can be made of suitable biocompatible material, such as spring steel. Elgiloy is another material which could possibly be used to manufacture the basket. Also, very elastic polymers could be used to manufacture the basket.

The strut size is often very small, so the tubing from which the basket is made may have a small diameter. Typically, the tubing has an outer diameter on the order of about 0.020-0.040 inch in the unexpanded condition. Also, the basket can be cut from large diameter tubing. Fittings are attached to both ends of the lased tube to form the final basket geometry. The wall thickness of the tubing is usually about 0.076 mm (0.001-0.010 inch). As can be appreciated, the strut width and/or depth at the bending points are less. For baskets deployed in a body lumen, such as with PTA applications, the dimensions of the tubing may be correspondingly larger. While it is preferred that the basket be made from laser cut tubing, those skilled in the art realize that the basket can be laser cut from a flat sheet and then rolled up in a tubular configuration with the longitudinal seam welded.

Generally, the tubing is put in a rotatable collet fixture of a machine controlled mandrel for positioning the tubing relative to a laser. According to machine encoded instructions, the tubing is rotated and moved longitudinally relative to the laser, which is also machine controlled. The laser selectively removes the material from the tubing by ablation and a pattern of openings is cut into the tube. The basket can thus be laser cut much like a stent is laser cut. Details on how the tubing can be cut by a laser are found, for example, in U.S. Pat. Nos. 5,759,192 (Saunders), 5,780,807 (Saunders), and 6,131,266 (Saunders), whose contents are hereby incorporated by reference.

The polymeric material which can be used to create the filter element include, but is not limited to, polyurethane and Gortex, both commercially available materials. Other possible suitable materials include ePTFE. The material can be elastic or inelastic. The wall thickness of the filter element is preferably about 0.00050-0.0050 inch. The wall thickness may vary depending on the particular material selected. The material can be shaped into a cone or similar shape using blow mold technology or dip molding technology.

Perfusion openings in the filter element can be any number of shapes or sizes. A laser, a heated rod, or other methods can be used to create to perfusion openings in the filter material. The openings would, of course, be properly sized to prevent passage of the embolic debris. The perfusion openings can be lased preferably into a spiral pattern or some similar pattern that aids in the re-wrapping of the filter media during closure of the device. Additionally, the filter material can have a "set" put in it much like the "set" used in dilatation balloons to make the filter element re-wrap more easily when transitioning into the collapsed state.

The restraining sheath can be made from a polymeric material such as cross-linked HDPE. The sheath can alternatively be made from a material such as polyolefin, which has sufficient strength to hold the compressed filter assembly, and which has a relatively low coefficient of friction to minimize any drag between the filter assembly and the sheath. Friction can be further reduced by applying a coat of silicone lubricant, such as MICROGLIDE®, to the inside surface of the restraining sheath before the sheath is placed over the filter assembly. Silicone also can be placed on the filter material as well.

Further modifications and improvements can be made to the devices and methods disclosed herein without departing from the scope of the present invention. Accordingly, it is not intended that the invention be limited, except as by the appended claims.

We claim:

1. An embolic protection device that locks to any point along a guide wire, comprising:
   an elongated guide wire core, the core having a proximal end and a distal end;
   a first guide wire coil, the first guide wire coil having a proximal end and a distal end, wherein the first guide wire coil is constructed of a plurality of turns of wire radially disposed about the distal guide wire core, and the proximal end of the guide wire coil is affixed to the guide wire core adjacent to the distal end of the guide wire core;
   a filter assembly having a proximal end and a distal end, disposed on the guide wire core; and
   a second guide wire coil, the second guide wire coil having a proximal end and a distal end, wherein the second guide wire coil is constructed of a plurality of turns of wire, and the proximal end of the second guide wire coil is coupled to the distal end of the filter assembly, wherein the second guide wire coil is configured to overlay the first guide wire coil such that turns of the second guide wire coil interlace with turns from the first guide wire coil to lock the second guide wire coil to the first guide wire coil.

2. The embolic protection device of claim 1, wherein at least one of the turns of the second guide wire coil includes a heat shrinkable shape memory metal alloy.

3. The embolic protection device of claim 1, wherein the embolic protection device includes a guide wire locking component that includes at least one of a threaded engagement and a frictional engagement.

4. The embolic protection device of claim 1, wherein the embolic protection device includes a guide wire locking component that includes wire locking component includes a thrust bearing.

5. The embolic protection device of claim 1, wherein the embolic protection device includes a guide wire locking component that includes wire locking component includes a heat shrinkable shape memory polymer.

6. An embolic protection system for use in a patient, comprising:
   a guide wire having a core without stops;
   a filter assembly having a first end and a second end; and
   a locking component disposed on at least one of the ends of the filter assembly, the locking component having an expanded state and a contracted state;

wherein the locking component locks on the guide wire core when the locking component is transformed from the expanded state to the contracted state; and the guide wire core includes a distal coil, and the locking component includes a locking coil at least partially overlying the distal coil such that turns of the locking coil and the distal coil interlace and engage.

7. The embolic protection system of claim 6, wherein the locking component includes a shape memory polymer.

8. The embolic protection system of claim 7, wherein the locking component includes a high glass temperature polymer and a low glass temperature polymer.

9. The embolic protection system of claim 6, wherein the locking component includes a heat shrink polymer.

10. The embolic protection system of claim 6, wherein the locking component includes a shrinkable polymer triggered by acidity change.

11. The embolic protection system of claim 6, wherein the locking component includes a shape memory nickel-titanium alloy having an austenitic contracted state and a martensitic expanded state.

12. The embolic protection system of claim 11, wherein a transition temperature of the shape memory nickel-titanium alloy is set to about body temperature of the patient.

* * * * *

UNITED STATES PATENT AND TRADEMARK OFFICE
CERTIFICATE OF CORRECTION

| | | |
|---|---|---|
| PATENT NO. | : 7,678,129 B1 | |
| APPLICATION NO. | : 10/805455 | |
| DATED | : March 16, 2010 | |
| INVENTOR(S) | : Douglas H. Gesswein et al. | |

It is certified that error appears in the above-identified patent and that said Letters Patent is hereby corrected as shown below:

Title page, (75), Inventors, delete "Robert C. Hazelden" insert instead --Robert C. Hayzelden--.

Signed and Sealed this
Fifth Day of April, 2011

David J. Kappos
*Director of the United States Patent and Trademark Office*